(12) United States Patent
Park et al.

(10) Patent No.: US 11,474,108 B2
(45) Date of Patent: Oct. 18, 2022

(54) MAM-SPECIFIC FLUORESCENCE CALCIUM SENSOR AND USE THEREOF

(71) Applicant: POSTECH ACADEMY-INDUSTRY FOUNDATION, Pohang-si (KR)

(72) Inventors: Sang Ki Park, Pohang-si (KR); Yeong Jun Suh, Gwangju (KR); Seung Hyun Kim, Busan (KR)

(73) Assignee: POSTECH ACADEMY—INDUSTRY FOUNDATION, Pohang-si (KR)

( * ) Notice: Subject to any disclaimer, the term of this patent is extended or adjusted under 35 U.S.C. 154(b) by 33 days.

(21) Appl. No.: 16/316,087

(22) PCT Filed: Nov. 22, 2017

(86) PCT No.: PCT/KR2017/013340
§ 371 (c)(1),
(2) Date: Jan. 8, 2019

(87) PCT Pub. No.: WO2018/097593
PCT Pub. Date: May 31, 2018

(65) Prior Publication Data
US 2021/0318325 A1 Oct. 14, 2021

(30) Foreign Application Priority Data

Nov. 25, 2016 (KR) .................. 10-2016-0157967
Nov. 17, 2017 (KR) .................. 10-2017-0154218

(51) Int. Cl.
*G01N 33/58* (2006.01)
*G01N 21/64* (2006.01)
*G01N 33/84* (2006.01)
*G01N 33/68* (2006.01)

(52) U.S. Cl.
CPC .......... *G01N 33/582* (2013.01); *G01N 21/64* (2013.01); *G01N 33/6803* (2013.01); *G01N 33/84* (2013.01)

(58) Field of Classification Search
CPC .... G01N 21/64; G01N 33/542; G01N 33/582; G01N 33/6803; G01N 33/84
See application file for complete search history.

(56) References Cited

U.S. PATENT DOCUMENTS

2005/0208624 A1    9/2005 Miyawaki et al.

OTHER PUBLICATIONS

English translation of the Written Opinion of the International Searching Authority for PCT/KR2017/013340 dated Aug. 3, 2018.*
Csordás et al., "Imaging Interorganelle Contacts and Local Calcium Dynamics at the ER-Mitochondrial Interface," Mol. Cell, 2010, vol. 39, issue 1, pp. 121-132.*
A printout retrieved from https://www.ebi.ac.uk/Tools/st/emboss_transeq/ on Feb. 22, 2022.*
A printout retrieved from https://www.cbi.ac.uk/Tools/services/web/toolresult.cbi?jobId=emboss transeq- on Feb. 22, 2022.*
Miller et al., "Bimolecular Fluorescence Complementation (BiFC) Analysis: Advances and Recent Applications for Genome-Wide Interaction Studies," J. Mol. Biol., 2015, vol. 427, No. 11, pp. 2039-2055.*
Spencer C. Alford et al., "Dimerization-Dependent Green and Yellow Fluorescent Proteins", ACS Synth Biol., 2012, vol. 1, pp. 569-575.
Ashley A. Rowland et al., "Endoplasmic reticulum-mitochondria contacts: function of the junction", Nat Rev Mol Cell Biol., 2012, vol. 13, pp. 607-625.
NCBI, GenBank Accession No. XM_017313703.1, Jun. 22, 2016.
NCBI, GenBank Accession No. BC152925.1, Dec. 3, 2007.
NCBI, GenBank Accession No. AK141611.1, Oct. 6, 2010.
NCBI, GenBank Accession No. KP230401.1, Apr. 29, 2015.
Rosario Rizzuto et al., "Ca2+ transfer from the ER to mitochondria: When, how and why", Biochimica et Biophysica Acta, vol. 1787, 2009, pp. 1342-1351.

* cited by examiner

*Primary Examiner* — Galina M. Yakovleva
(74) *Attorney, Agent, or Firm* — Lex IP Meister, PLLC

(57) ABSTRACT

The present disclosure relates to a Mitochondria-Associated endoplasmic reticulum Membrane (MAM)-specific fluorescence calcium sensor and the use thereof. The present disclosure can surmount the limitations of a conventional technique in that verification of calcium migration through MAM requires separate measurements of calcium ion concentrations within ER and mitochondria and situational explanations of the phenomena, and can directly measure concentrations in the paths through which calcium ions move to exclude influences on calcium ion changes through numerous different calcium ion channels existing in mitochondria, thereby providing a convenient and accurate MAM-specific calcium ion sensor.

12 Claims, 15 Drawing Sheets

Specification includes a Sequence Listing.

[FIG. 1A]
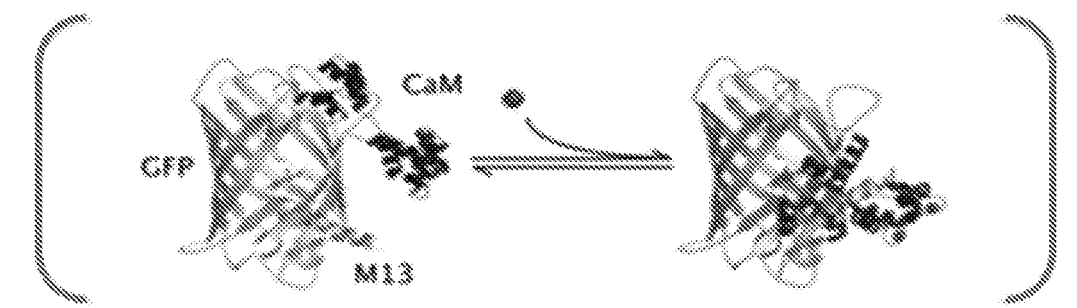
GCaMP: Green fluorescent calcium ion sensor
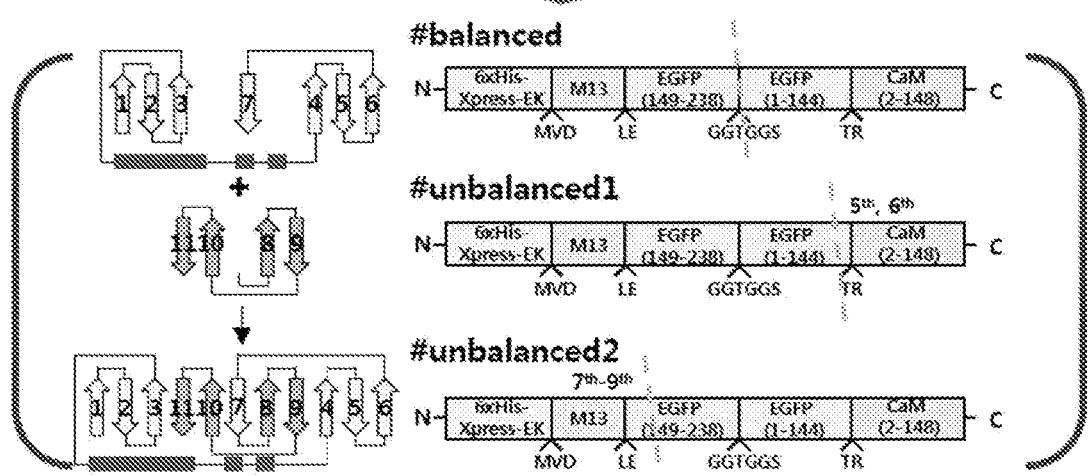
Production of a functional pair of split Calcium sensor
Based on the molecular structure of GCaMP
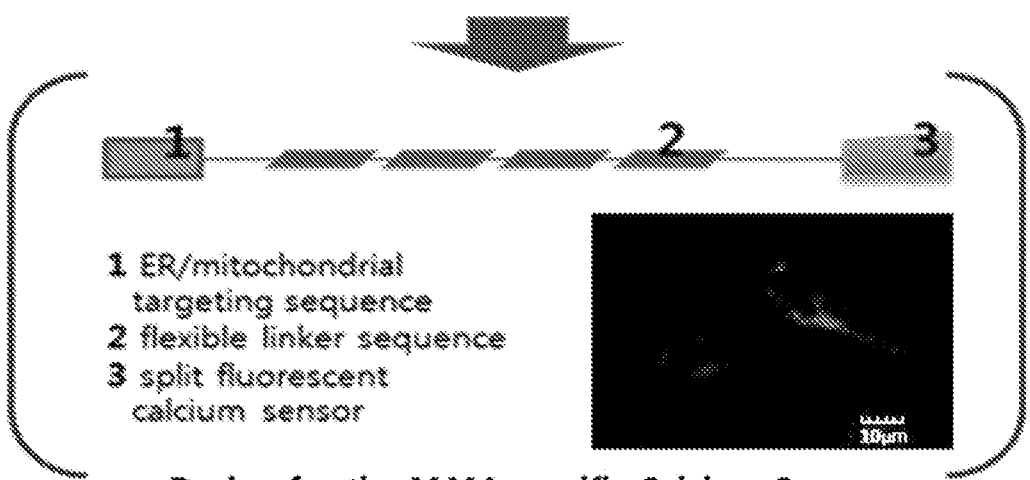
1 ER/mitochondrial targeting sequence
2 flexible linker sequence
3 split fluorescent calcium sensor
Design for the MAM-specific Calcium Sensor

[FIG.1B]
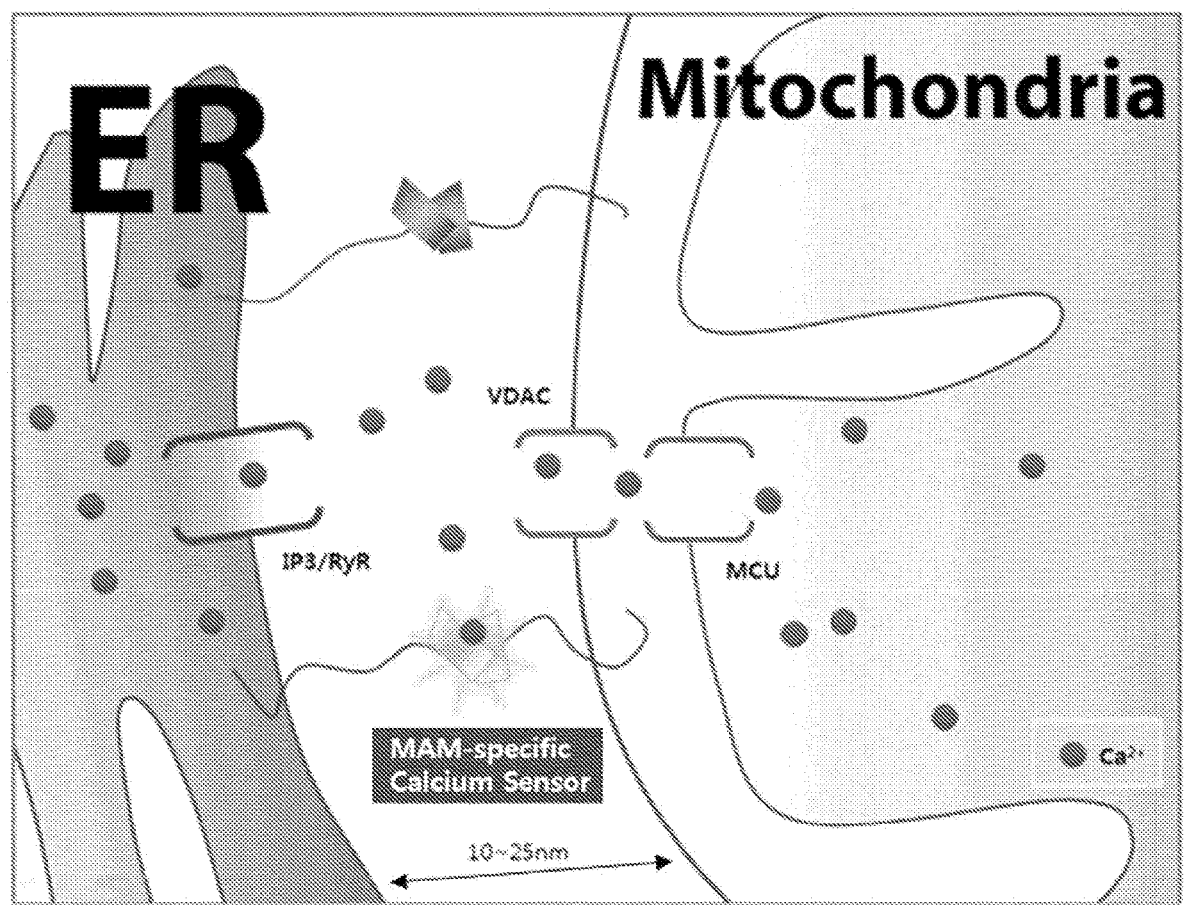

[FIG. 2]
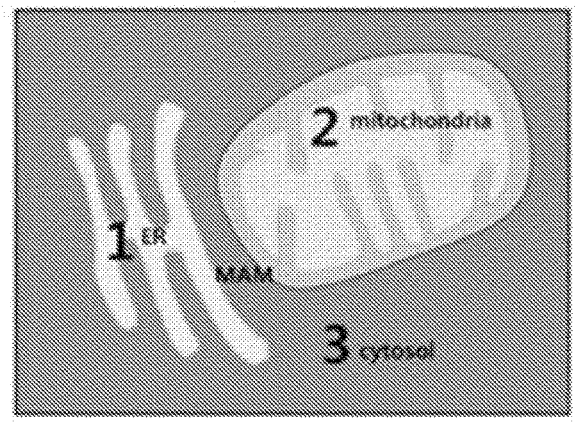
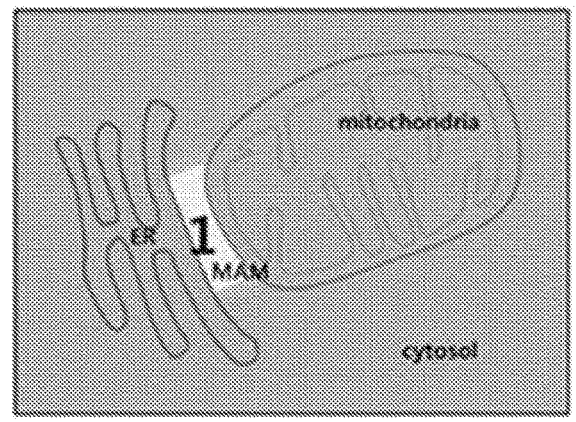

[FIG. 3A]
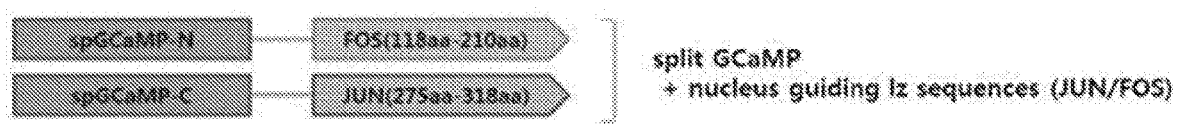

[FIG. 3B]
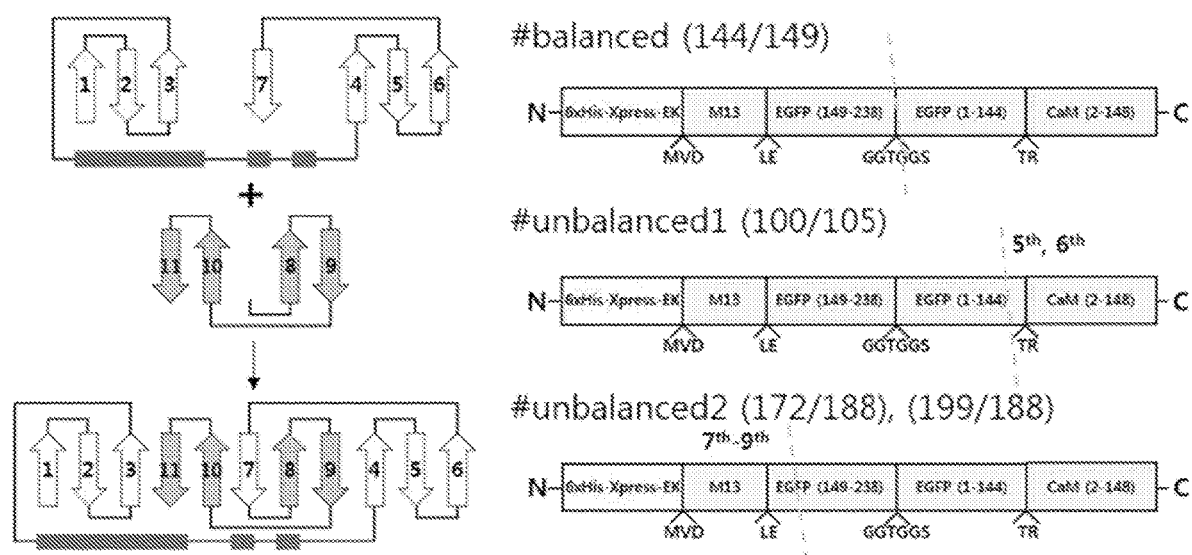

[FIG. 4]
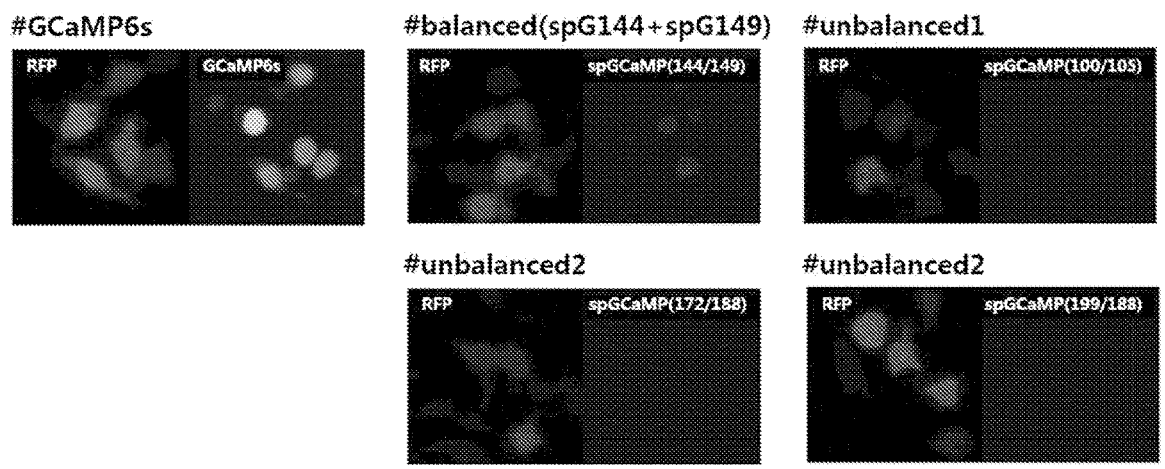

[FIG. 5]
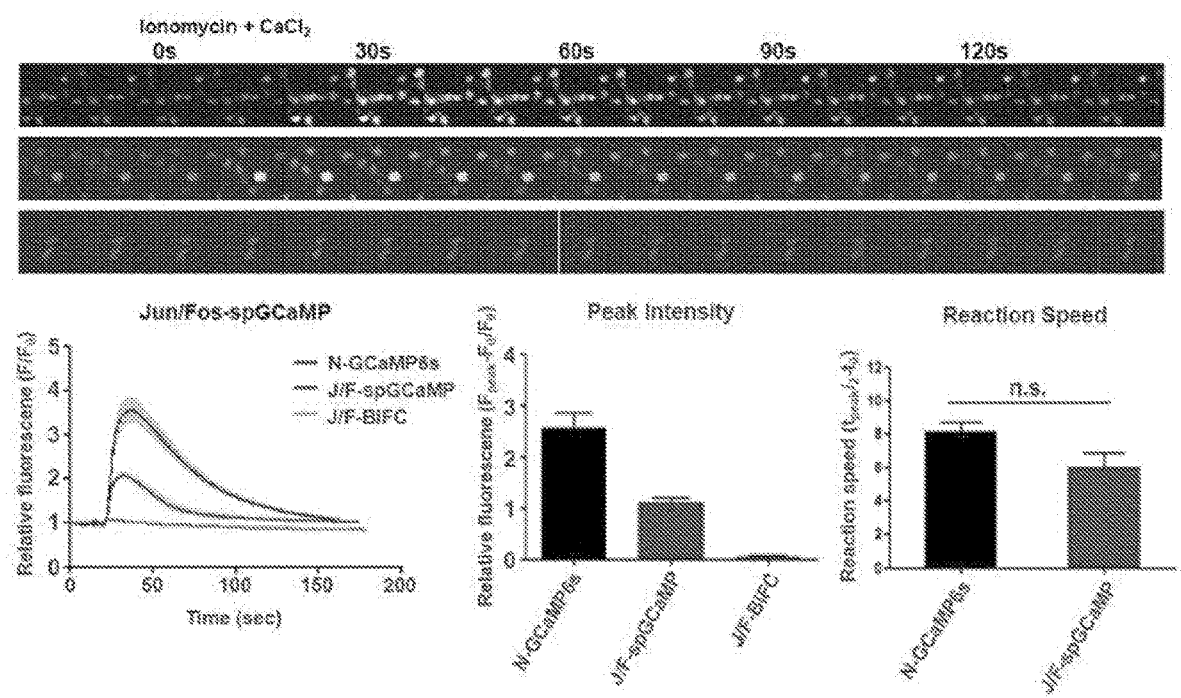

[FIG. 6A]
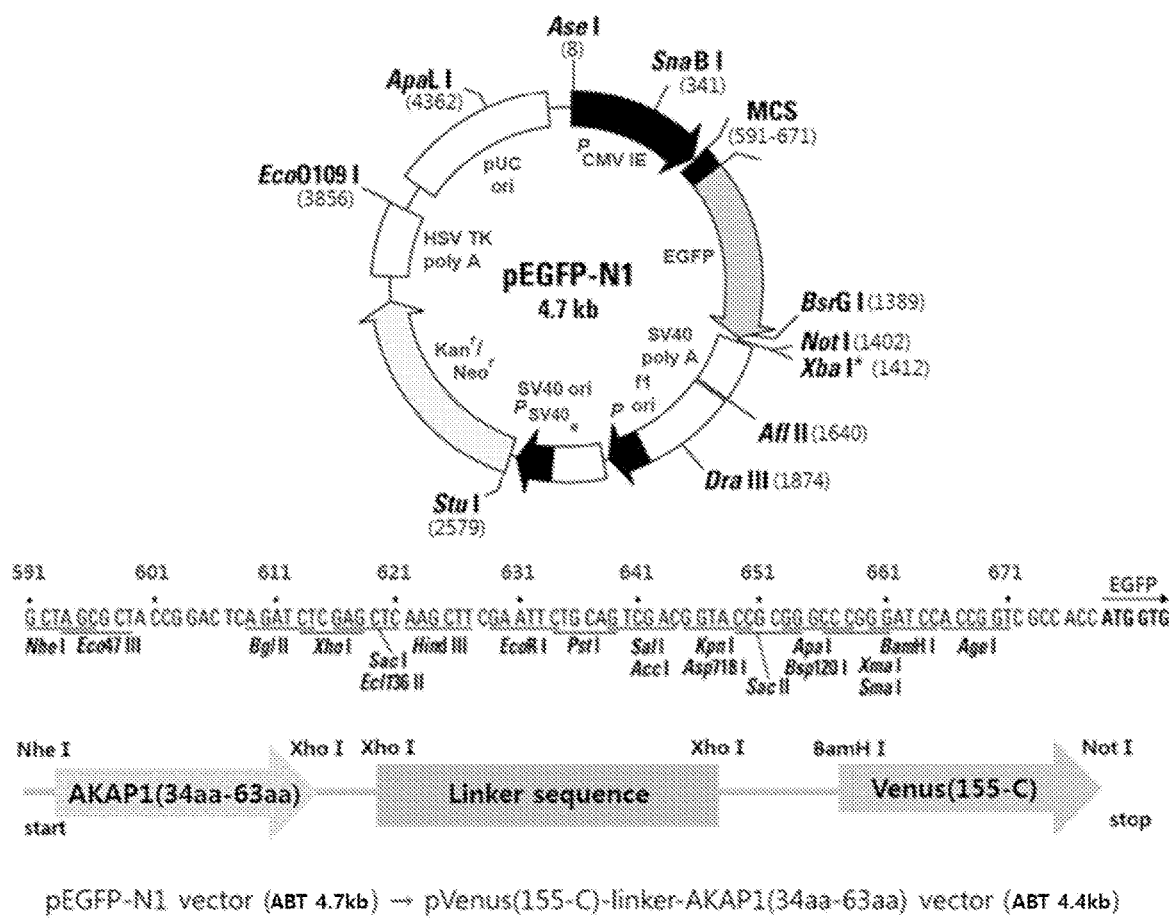

[FIG. 6B]
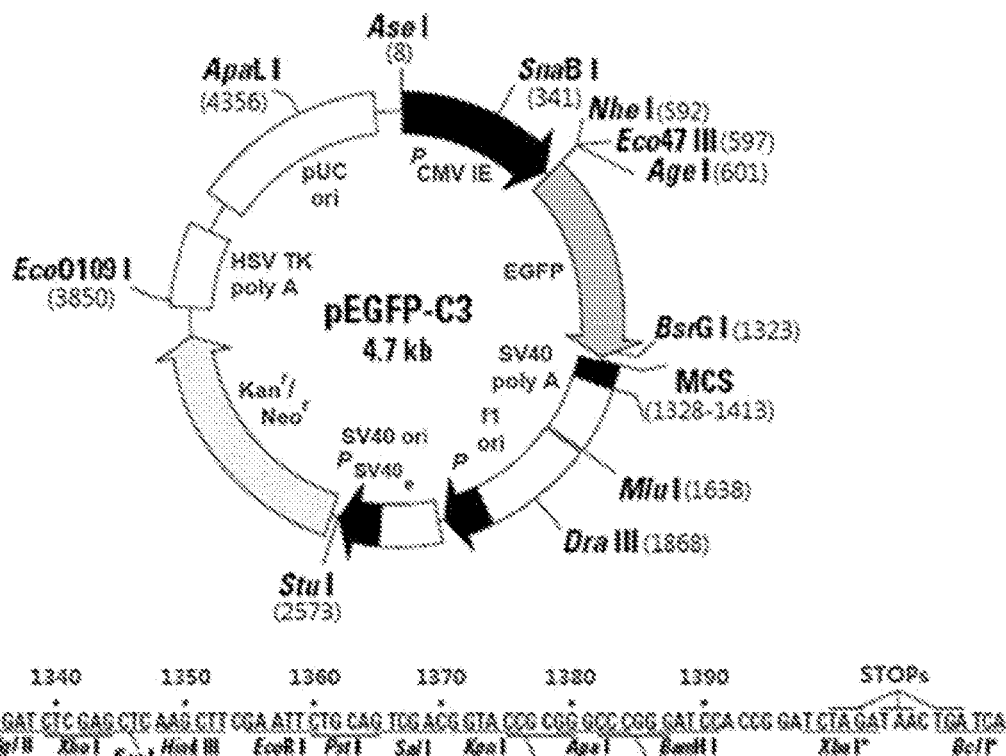

[FIG. 7A]
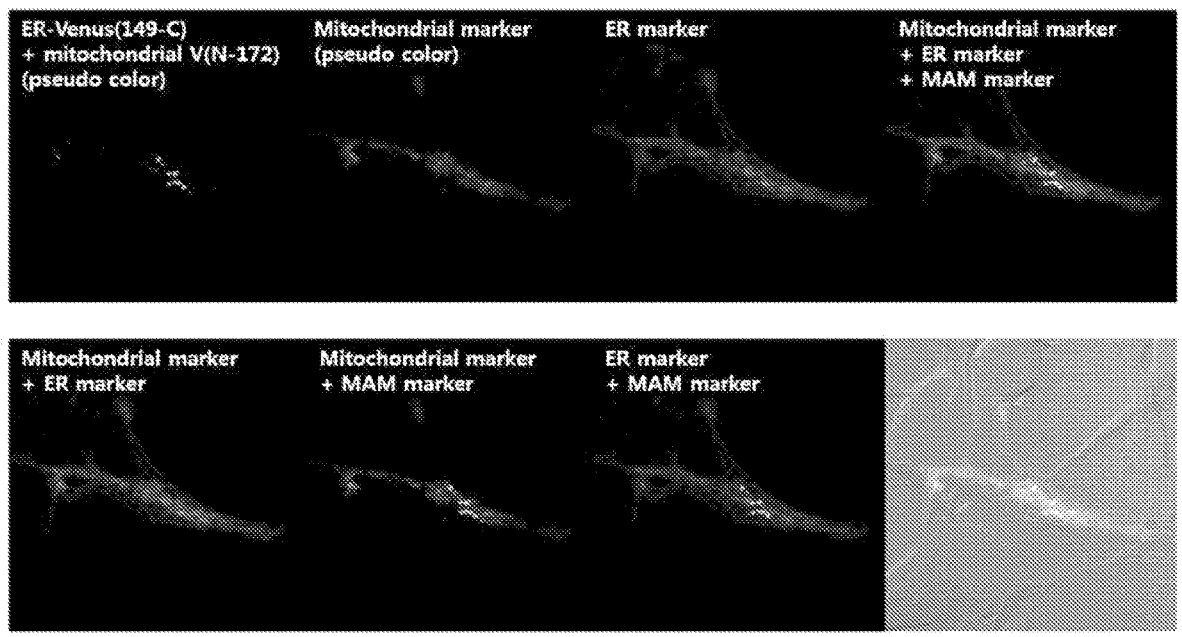

[FIG. 7B]
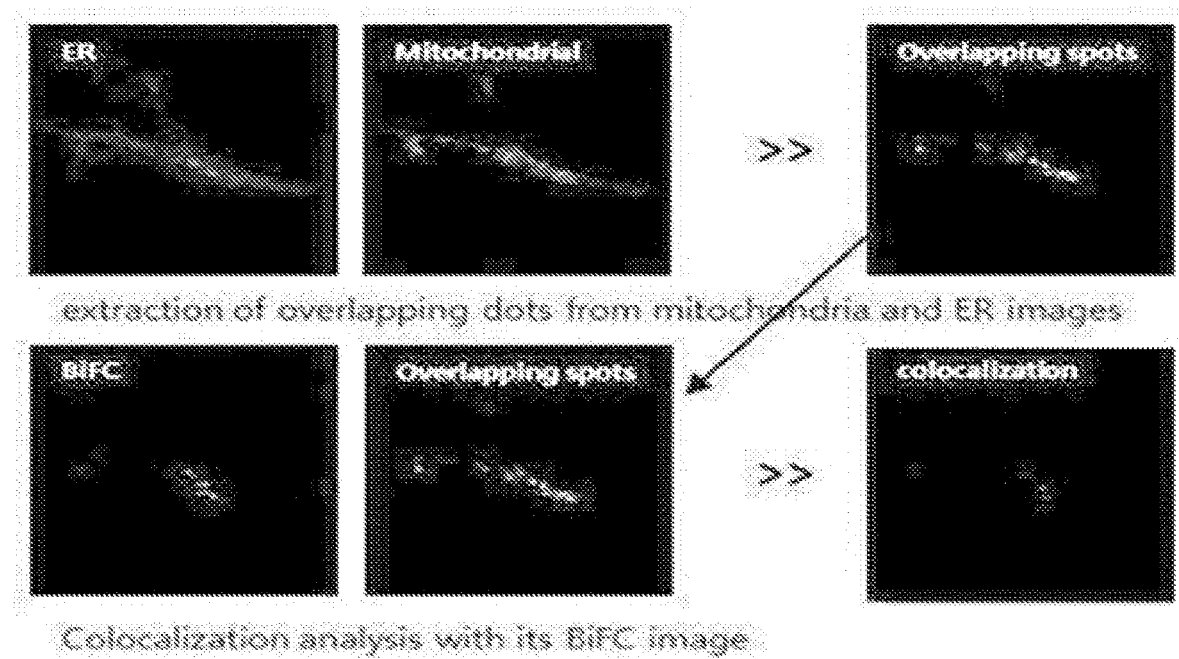
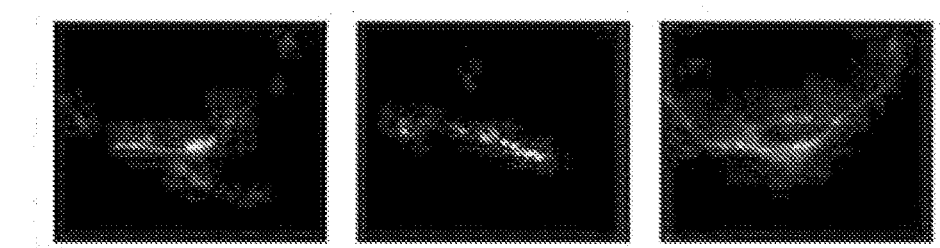
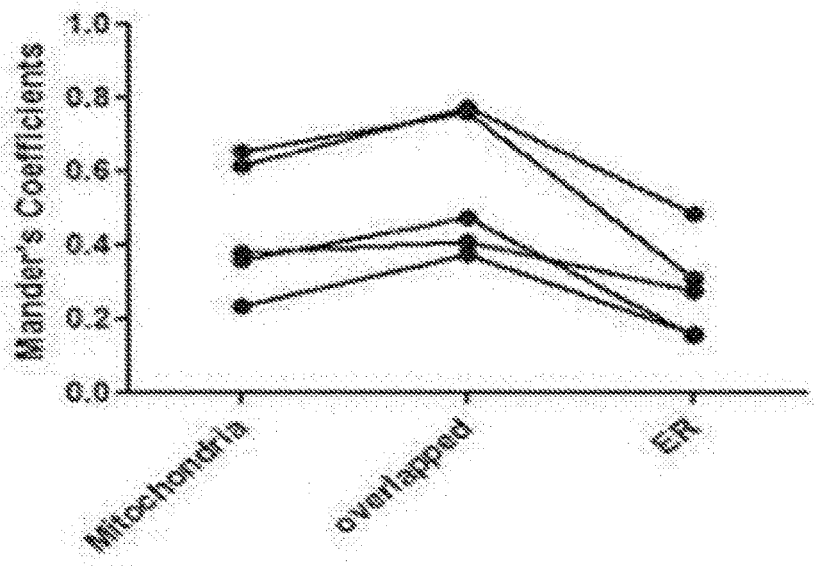

[FIG. 7C]
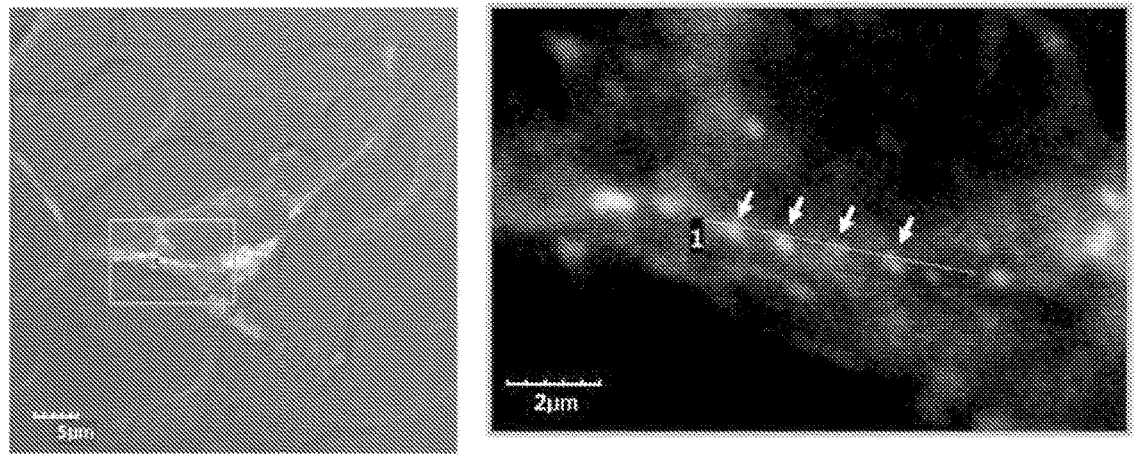
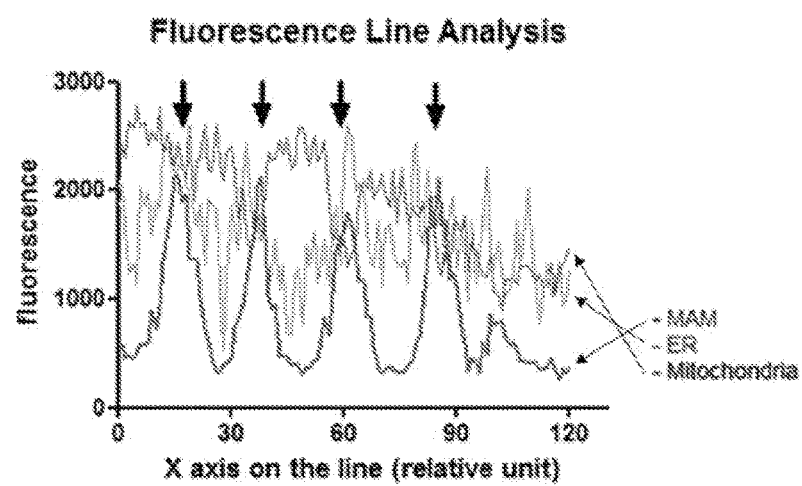

[FIG. 8A]
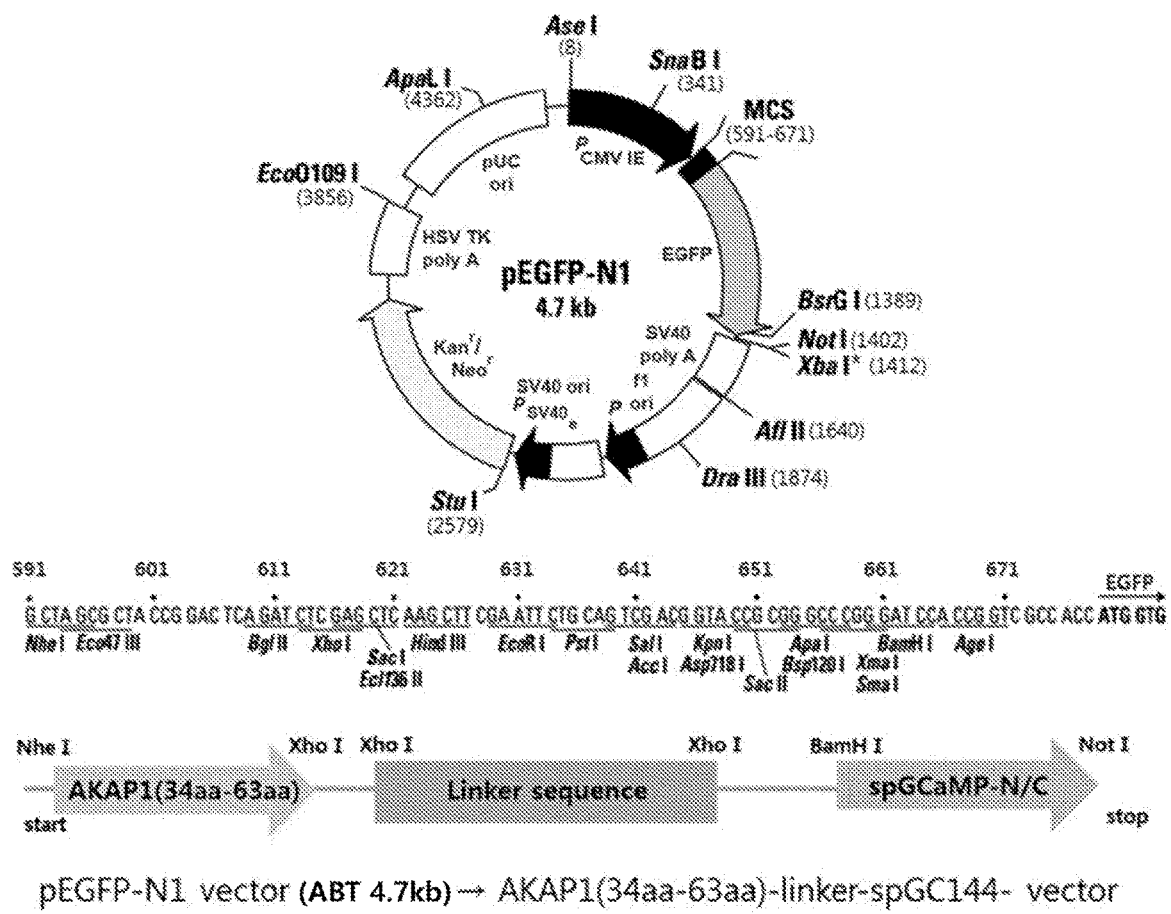

[FIG. 8B]
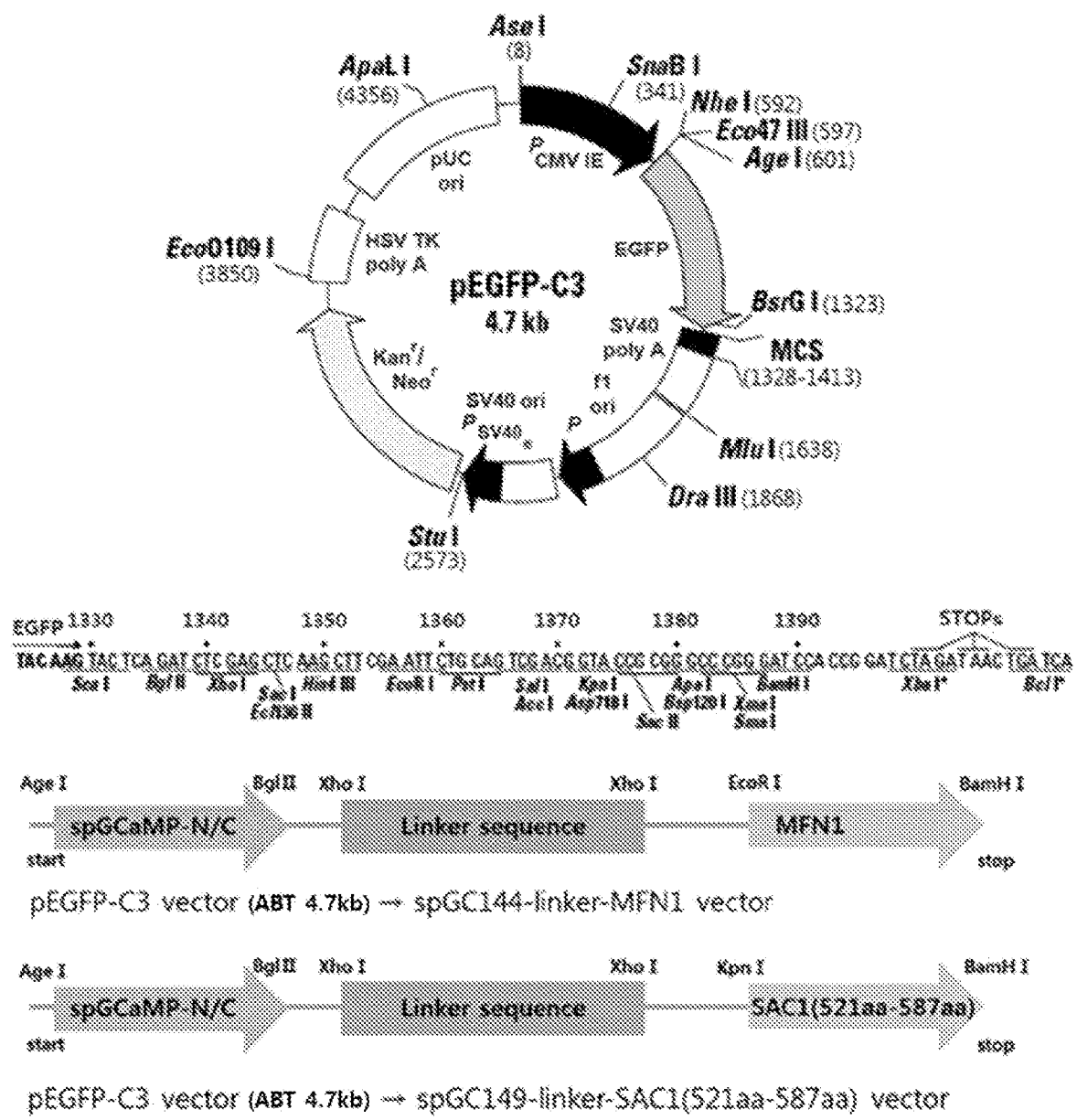

[FIG. 9]
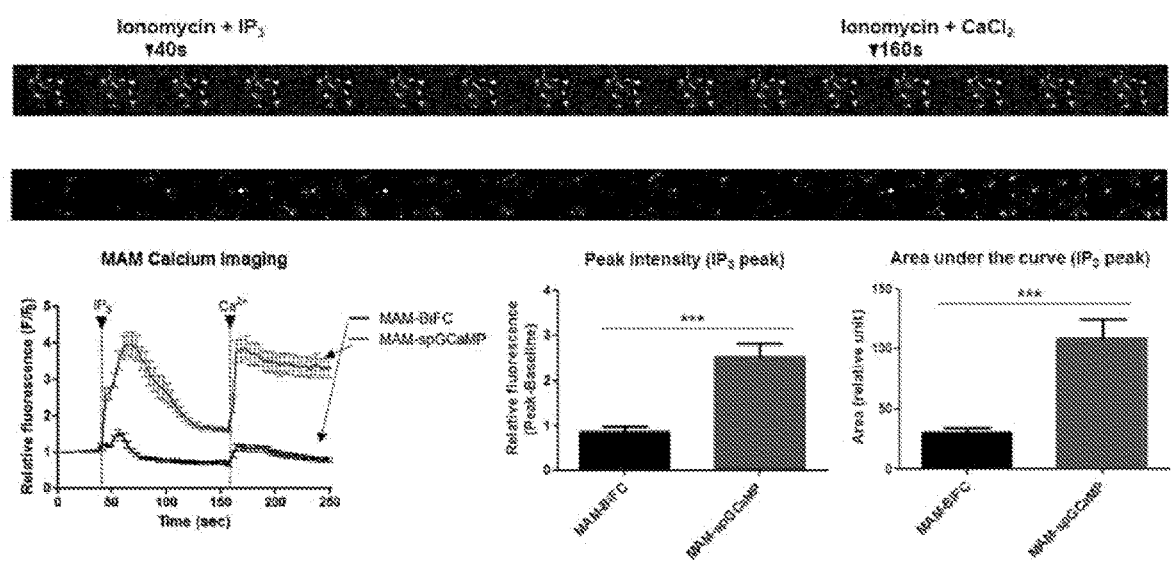

SEQUENCE LISTING

<160> NUMBER OF SEQ ID NOS: 35

<210> SEQ ID NO 1
<211> LENGTH: 204
<212> TYPE: DNA
<213> ORGANISM: Mus musculus
<220> FEATURE:
<221> NAME/KEY: misc_feature
<222> LOCATION: (1)..(204)
<223> OTHER INFORMATION: Sac1(521aa-587aa)

<400> SEQUENCE: 1

```
ttcctggcgt tgcctatcat catggttgtt gccttttcaa tgtgcatcat ctgtttgctt      60
atggctggtg acacttggac agaaacactg gcatatgtcc tcttctgggg agttgcaagc     120
attggaacat tttttattat tctttacaat ggcaaagatt ttgttgatgc tcccagactg     180
gtccagaaag aaaagataga ctga                                            204
```

<210> SEQ ID NO 2
<211> LENGTH: 90
<212> TYPE: DNA
<213> ORGANISM: Mus musculus
<220> FEATURE:
<221> NAME/KEY: misc_feature
<222> LOCATION: (1)..(90)
<223> OTHER INFORMATION: AKAP1(34aa-63aa)

<400> SEQUENCE: 2

```
atggcaatcc agttgcgttc gctcttcccc ttggcgttgc ccggaatgct ggccctcctt      60
ggctggtggt ggttttctc tcgtaaaaaa                                        90
```

<210> SEQ ID NO 3
<211> LENGTH: 2226
<212> TYPE: DNA
<213> ORGANISM: Mus musculus
<220> FEATURE:
<221> NAME/KEY: misc_feature
<222> LOCATION: (1)..(2226)
<223> OTHER INFORMATION: MFN1

<400> SEQUENCE: 3

```
atggcagaaa cggtatctcc actgaagcac tttgtgctgg caaagaaagc catcactgca      60
atcttcggcc agttactgga gtttgttact gagggctcac attttgttga agcaacatac     120
aggaatccag aacttgatcg aatagcatcc gaggatgatc tggtggaaat acagggctac     180
agaaacaagc ttgctgtcat tggggaggtg ctgtctcgga gacatatgaa ggtggcattt     240
tttggcagga caagtagtgg caagagctct gtcatcaatg caatgctgtg ggataaagtc     300
ctccccagcg ggattggtca cacaaccaac tgcttcctga gtgtcgaggg gaccgatgga     360
gataaagcct accttatgac cgaagggtca gatgaaaaga aagtgtgaa gactgttaat     420 cagctggccc atgccctcca tatggataaa gacttgaaag ctggctgtct tgtgcatgta     480
ttttggccca agcaaaaatg tgccctcttg agagatgacc tggttttagt agacagccca     540
ggtacagatg tcaccacaga gctggatatc tggattgata gttttgcct tgatgctgat     600 gtctttgttt tggttgcaaa ctcggaatca acactgatga cacggagaa acatttttc     660 cataaggtga atgagcggct ctccaagccc aacatcttca ttctgaataa ccgttgggat     720
gcttctgctt cggagccgga gtacatggag gatgtgcgca cagcacat ggagagatgt     780 cttcacttct tggtagaaga gctcaaggtt gtaagtccgt cggaagctcg gaatcggatc     840
tttttgtttt cagccaagga agttctcaac tccagaaagc ataaagctca ggggatgcca     900
```

```
gaaggtggtg gggcacttgc agaaggattt caagcaagat tacaggagtt tcaaaatttt    960
gaacaaactt ttgaggagtg tatctcgcag tcagcagtga aaacaaagtt tgaacagcac   1020
actatcagag ctaaacagat actagacact gtgaaaaaca tactggactc agtaaacgtg   1080
gcagcagcag agaagagggt ttattcaatg gaagagaggg aagaccaaat cgatagactg   1140
gactttatcc gaaaccagat gaacctttta acactggatg ttaagaagaa gatcaaggag   1200
gtcacggagg aggtggcaaa caaggtttct tgtgcaatga cagatgaaat tgtcgacta    1260 tctgttttgg ttgatgagtt ttgttctgag tttcatccta cccccagtgt actgaaagtg   1320
tataagagtg agttaaataa gcacatagaa gatggcatgg aagaaatttt ggctgatcgg   1380
tgtaccaatg aagtcaatgc ctccattctt caatctcagc aagaaatcat cgaaaacttg   1440
aagccactac ttccagctgg tatacagaat aaacttcata cattaatccc ttgcaaaaag   1500
tttgacctca gctatgatct caattgccac aagctgtgtt cggattttca agaggacatt   1560
gtgtttcggt tttccctggg ctggtcttcc cttgtacatc gattcctggg ttccacaaat   1620
gcacagaggg tgctgctcgg gctgtcagag cccatctttc aggtccctag atctttagct   1680
tcaactccta ctgctccttc taacccagca gccccggata tgcagcccca ggaggagctc   1740
atgatcaccc tgatcacagg attggcgtcc ctcacgtcga aacctccat gggcatcatc    1800 gttgttgggg gcgtgatttg gaaaacagtg ggctggaaac taatctctgt caccttaagt   1860
atgtacggag ctctgtacct ttatgagagg ctgacgtgga cgacccgtgc gaaagagaga   1920
gcgtttaagc agcagtttgt aaactatgca accgagaagc tgcagatgat tgtgagcttc   1980
accagtgcaa actgcagcca ccaagtacag caagaaatgg ccactacttt tgctcgactg   2040
tgccaacaag ttgatgttac tcagaaacat ctggaagagg aaattgcaag attatccaaa   2100
gagatagacc aactggagaa aatacagaac aactcaaagc tcttaagaaa taaagctgtt   2160
caacttgaaa gtgagctgga gattttttcg aagcagtttc tacacccgag cagtggagaa   2220
tcctaa                                                              2226

<210> SEQ ID NO 4
<211> LENGTH: 60
<212> TYPE: DNA
<213> ORGANISM: Artificial
<220> FEATURE:
<223> OTHER INFORMATION: linker

<400> SEQUENCE: 4
gacccaacca ggtcagcgaa ttctggagca ggagcaggag caggagcaat actctcccgt     60

<210> SEQ ID NO 5
<211> LENGTH: 450
<212> TYPE: DNA
<213> ORGANISM: Mus musculus
<220> FEATURE:
<221> NAME/KEY: misc_feature
<222> LOCATION: (1)..(450)
<223> OTHER INFORMATION: spGCaMP144

<400> SEQUENCE: 5
atgggttctc atcatcatca tcatcatggt atggctagca tgactggtgg acagcaaatg     60
ggtcgggatc tgtacgacga tgacgataag gatctcgcca ccatggtcga ctcatcacgt    120
cgtaagtgga ataagacagg tcacgcagtc agagctatag gtcggctgag ctcactcgag    180
aacgtctata tcaaggccga caagcagaag aacggcatca aggcgaactt ccacatccgc    240
```

```
cacaacatcg aggacggcgg cgtgcagctc gcctaccact accagcagaa caccccatc      300 ggcgacggcc ccgtgctgct gcccgacaac cactacctga gcgtgcagtc caaactttcg      360
aaagacccca acgagaagcg cgatcacatg gtcctgctgg agttcgtgac cgccgccggg      420
atcactctcg gcatggacga gctgtacaag                                       450

<210> SEQ ID NO 6
<211> LENGTH: 879
<212> TYPE: DNA
<213> ORGANISM: Mus musculus
<220> FEATURE:
<221> NAME/KEY: misc_feature
<222> LOCATION: (1)..(879)
<223> OTHER INFORMATION: spGCaMP149

<400> SEQUENCE: 6
gtgagcaagg gcgaggagct gttcaccggg gtggtgccca tcctggtcga gctggacggc       60
gacgtaaacg gccacaagtt cagcgtgtcc ggcgagggtg agggcgatgc cacctacggc      120
aagctgaccc tgaagttcat ctgcaccacc ggcaagctgc ccgtgccctg gcccaccctc      180
gtgaccaccc tgacctacgg cgtgcagtgc ttcagccgct accccgacca catgaagcag      240
cacgacttct tcaagtccgc catgcccgaa ggctacatcc aggagcgcac catcttcttc      300
aaggacgacg gcaactacaa gacccgcgcc gaggtgaagt tcgagggcga caccctggtg      360
aaccgcatca gctgaaggg catcgacttc aaggaggacg gcaacatcct ggggcacaag      420
ctggagtaca acctgccgga ccaactgact gaagagcaga tcgcagaatt taaagaggct      480
ttctccctat tgacaagga cggggatggg acaataacaa ccaaggagct ggggacggtg       540
atgcggtctc tggggcagaa ccccacagaa gcagagctgc aggacatgat caatgaagta      600
gatgccgacg gtgacggcac aatcgacttc cctgagttcc tgacaatgat ggcaagaaaa      660
atgaaataca gggacacgga agaagaaatt agagaagcgt tcggtgtgtt tgataaggat      720
ggcaatggct acatcagtgc agcagagctt cgccacgtga tgacaaacct tggagagaag      780
ttaacagatg aagaggttga tgaaatgatc agggaagcag acatcgatgg ggatggtcag      840
gtaaactacg aagagtttgt acaaatgatg acagcgaag                            879

<210> SEQ ID NO 7
<211> LENGTH: 1431
<212> TYPE: DNA
<213> ORGANISM: Mus musculus
<220> FEATURE:
<221> NAME/KEY: misc_feature
<222> LOCATION: (1)..(1431)
<223> OTHER INFORMATION: GCaMP-NLS

<400> SEQUENCE: 7
atgggttctc atcatcatca tcatcatggt atggctagca tgactggtgg acagcaaatg       60
ggtcgggatc tgtacgacga tgacgataag gatctcgcca ccatggtcga ctcatcacgt      120
cgtaagtgga ataagacagg tcacgcagtc agagctatag gtcggctgag ctcactcgag      180
aacgtctata tcaaggccga caagcagaag aacggcatca aggcgaactt ccacatccgc      240
cacaacatcg aggacggcgg cgtgcagctc gcctaccact accagcagaa caccccatc      300 ggcgacggcc ccgtgctgct gcccgacaac cactacctga gcgtgcagtc caaactttcg      360
aaagacccca acgagaagcg cgatcacatg gtcctgctgg agttcgtgac cgccgccggg      420
atcactctcg gcatggacga gctgtacaag gcggtaccg agggagcat ggtgagcaag        480 ggcgaggagc tgttcaccgg ggtggtgccc atcctggtcg agctggacgg cgacgtaaac      540
```

```
ggccacaagt tcagcgtgtc cggcgagggt gagggcgatg ccacctacgg caagctgacc      600
ctgaagttca tctgcaccac cggcaagctg cccgtgccct ggcccaccct cgtgaccacc      660
ctgacctacg gcgtgcagtg cttcagccgc taccccgacc acatgaagca gcacgacttc      720
ttcaagtccg ccatgcccga aggctacatc caggagcgca ccatcttctt caaggacgac      780
ggcaactaca agacccgcgc cgaggtgaag ttcgagggcg acaccctggt gaaccgcatc      840
gagctgaagg gcatcgactt caaggaggac ggcaacatcc tggggcacaa gctggagtac      900
aacctgccgg accaactgac tgaagagcag atcgcagaat ttaaagaggc tttctcccta      960
tttgacaagg acggggatgg gacaataaca accaaggagc tggggacggt gatgcggtct     1020
ctggggcaga accccacaga agcagagctg caggacatga tcaatgaagt agatgccgac     1080
ggtgacggca caatcgactt ccctgagttc ctgacaatga tggcaagaaa aatgaaatac     1140
agggacacgg aagaagaaat tagagaagcg ttcggtgtgt tgataagga tggcaatggc      1200 tacatcagtg cagcagagct tcgccacgtg atgacaaacc ttggagagaa gttaacagat     1260
gaagaggttg atgaaatgat cagggaagca gacatcgatg gggatggtca ggtaaactac     1320
gaagagtttg tacaaatgat gacagcgaag gatccagatc caaaaaagaa gagaaaggta     1380
gatccaaaaa agaagagaaa ggtagatcca aaaaagaaga gaaaggtata a              1431

<210> SEQ ID NO 8
<211> LENGTH: 94
<212> TYPE: DNA
<213> ORGANISM: Artificial
<220> FEATURE:
<223> OTHER INFORMATION: part of pEGFP-N1 vector

<400> SEQUENCE: 8
gctagcgcta ccggactcag atctcgagct caagcttcga attctgcagt cgacggtacc       60
gcgggcccgg gatccaccgg tcgccaccat ggtg                                   94

<210> SEQ ID NO 9
<211> LENGTH: 90
<212> TYPE: DNA
<213> ORGANISM: Artificial
<220> FEATURE:
<223> OTHER INFORMATION: part of pEGFP-C3 vector

<400> SEQUENCE: 9
tacaagtact cagatctcga gctcaagctt cgaattctgc agtcgacggt accgcgggcc       60
cgggatccac cggatctaga taactgatca                                        90

<210> SEQ ID NO 10
<211> LENGTH: 31
<212> TYPE: DNA
<213> ORGANISM: Artificial
<220> FEATURE:
<223> OTHER INFORMATION: Fos-(118aa-210aa) forward primer

<400> SEQUENCE: 10
ccgggaattc tgggcagagc gcagagcatc g                                      31

<210> SEQ ID NO 11
<211> LENGTH: 34
<212> TYPE: DNA
<213> ORGANISM: Artificial
<220> FEATURE:
<223> OTHER INFORMATION: Fos-(118aa-210aa) reverse primer
```

<400> SEQUENCE: 11
cgcggatcct caaaggtcat cggggatctt gcag                          34

<210> SEQ ID NO 12
<211> LENGTH: 32
<212> TYPE: DNA
<213> ORGANISM: Artificial
<220> FEATURE:
<223> OTHER INFORMATION: Jun-(257aa-318aa) forward primer

<400> SEQUENCE: 12
ccggaattct gaaggcagag aggaagcgca tg                            32

<210> SEQ ID NO 13
<211> LENGTH: 30
<212> TYPE: DNA
<213> ORGANISM: Artificial
<220> FEATURE:
<223> OTHER INFORMATION: Jun-(257aa-318aa) reverse primer

<400> SEQUENCE: 13
cgcggatcct cagtggttca tgactttctg                               30

<210> SEQ ID NO 14
<211> LENGTH: 43
<212> TYPE: DNA
<213> ORGANISM: Artificial
<220> FEATURE:
<223> OTHER INFORMATION: spGC-N-terminus forward primer

<400> SEQUENCE: 14
gggaccggtg ccaccatggg ttctcatcat catcatcatc atg                43

<210> SEQ ID NO 15
<211> LENGTH: 32
<212> TYPE: DNA
<213> ORGANISM: Artificial
<220> FEATURE:
<223> OTHER INFORMATION: spGC149 reverse primer

<400> SEQUENCE: 15
ggaagatctg acttgtacag ctcgtccatg cc                            32

<210> SEQ ID NO 16
<211> LENGTH: 33
<212> TYPE: DNA
<213> ORGANISM: Artificial
<220> FEATURE:
<223> OTHER INFORMATION: spGC144 forward primer

<400> SEQUENCE: 16
gggaccggtg ccaccatggt gagcaagggc gag                           33

<210> SEQ ID NO 17
<211> LENGTH: 36
<212> TYPE: DNA
<213> ORGANISM: Artificial
<220> FEATURE:
<223> OTHER INFORMATION: spGC-C-terminus reverse primer

<400> SEQUENCE: 17
ggaagatctg acttcgctgt catcatttgt acaaac                        36

<210> SEQ ID NO 18
<211> LENGTH: 32

<210> SEQ ID NO 18
<211> LENGTH: 32
<212> TYPE: DNA
<213> ORGANISM: Artificial
<220> FEATURE:
<223> OTHER INFORMATION: spGC100 reverse primer

<400> SEQUENCE: 18
ggaagatctg agaagaagat ggtgcgctcc tg                          32

<210> SEQ ID NO 19
<211> LENGTH: 36
<212> TYPE: DNA
<213> ORGANISM: Artificial
<220> FEATURE:
<223> OTHER INFORMATION: spGC105 forward primer

<400> SEQUENCE: 19
gggaccggtg ccaccatgta caagacccgc gccgag                      36

<210> SEQ ID NO 20
<211> LENGTH: 30
<212> TYPE: DNA
<213> ORGANISM: Artificial
<220> FEATURE:
<223> OTHER INFORMATION: spGC188 reverse primer

<400> SEQUENCE: 20
ggaagatctg agatgggggt gttctgctgg                             30

<210> SEQ ID NO 21
<211> LENGTH: 34
<212> TYPE: DNA
<213> ORGANISM: Artificial
<220> FEATURE:
<223> OTHER INFORMATION: spGC172 forward primer

<400> SEQUENCE: 21
gggaccggtg ccaccatgga cggcggcgtg cagc                        34

<210> SEQ ID NO 22
<211> LENGTH: 39
<212> TYPE: DNA
<213> ORGANISM: Artificial
<220> FEATURE:
<223> OTHER INFORMATION: (spGC199)-Jun(257aa-318aa) vector

<400> SEQUENCE: 22
gggaccggtg ccaccatgca ctacctgagc gtgcagtcc                   39

<210> SEQ ID NO 23
<211> LENGTH: 34
<212> TYPE: DNA
<213> ORGANISM: Artificial
<220> FEATURE:
<223> OTHER INFORMATION: AKAP1-(34aa-63aa) forward primer

<400> SEQUENCE: 23
ctagctagcc accatggcaa tccagttgcg ttcg                        34

<210> SEQ ID NO 24
<211> LENGTH: 39
<212> TYPE: DNA
<213> ORGANISM: Artificial
<220> FEATURE:
<223> OTHER INFORMATION: AKAP1-(34aa-63aa) reverse primer

<400> SEQUENCE: 24
ccgctcgagt tttttacgag agaaaaacca ccaccagcc                   39

<210> SEQ ID NO 25
<211> LENGTH: 37
<212> TYPE: DNA
<213> ORGANISM: Artificial
<220> FEATURE:
<223> OTHER INFORMATION: Venus155-N1 forward primer

<400> SEQUENCE: 25
cgcggatccc accatgaagc agaagaacgg catcaag                     37

<210> SEQ ID NO 26
<211> LENGTH: 38
<212> TYPE: DNA
<213> ORGANISM: Artificial
<220> FEATURE:
<223> OTHER INFORMATION: Venus155-N1 reverse primer

<400> SEQUENCE: 26
aaatatgcgg ccgctttact tgtacagctc gtccatgc                    38

<210> SEQ ID NO 27
<211> LENGTH: 75
<212> TYPE: DNA
<213> ORGANISM: Artificial
<220> FEATURE:
<223> OTHER INFORMATION: linker oligo DNA
<220> FEATURE:
<221> NAME/KEY: repeat_unit
<222> LOCATION: (10)..(69)

<400> SEQUENCE: 27
ccgctcgagg acccaaccag gtcagcgaat tctggagcag gagcaggagc aggagcaata   60
ctctcccgtg tcgac                                             75

<210> SEQ ID NO 28
<211> LENGTH: 35
<212> TYPE: DNA
<213> ORGANISM: Artificial
<220> FEATURE:
<223> OTHER INFORMATION: MFN1 forward primer

<400> SEQUENCE: 28
ccggaattct ggcagaaacg gtatctccac tgaag                       35

<210> SEQ ID NO 29
<211> LENGTH: 31
<212> TYPE: DNA
<213> ORGANISM: Artificial
<220> FEATURE:
<223> OTHER INFORMATION: MFN1 reverse primer

<400> SEQUENCE: 29
cgcggatcct taggattctc cactgctcgg g                           31

<210> SEQ ID NO 30
<211> LENGTH: 33
<212> TYPE: DNA
<213> ORGANISM: Artificial
<220> FEATURE:
<223> OTHER INFORMATION: Venus N172-C3 forward primer

<400> SEQUENCE: 30
gggaccggtg ccaccatggt gagcaagggc gag                         33

```
<210> SEQ ID NO 31
<211> LENGTH: 30
<212> TYPE: DNA
<213> ORGANISM: Artificial
<220> FEATURE:
<223> OTHER INFORMATION: Venus N172-C3 reverse primer

<400> SEQUENCE: 31
ggaagatctg actcgatgtt gtggcggatc                                          30

<210> SEQ ID NO 32
<211> LENGTH: 31
<212> TYPE: DNA
<213> ORGANISM: Artificial
<220> FEATURE:
<223> OTHER INFORMATION: SAC1-(521aa-587aa) forward primer

<400> SEQUENCE: 32
cggggtaccg ttcctggcgt tgcctatcat c                                        31

<210> SEQ ID NO 33
<211> LENGTH: 36
<212> TYPE: DNA
<213> ORGANISM: Artificial
<220> FEATURE:
<223> OTHER INFORMATION: SAC1-(521aa-587aa) reverse primer

<400> SEQUENCE: 33
cgcggatcct cagtctatct tttctttctg gaccag                                   36

<210> SEQ ID NO 34
<211> LENGTH: 39
<212> TYPE: DNA
<213> ORGANISM: Artificial
<220> FEATURE:
<223> OTHER INFORMATION: Venus149C-C3 forward primer

<400> SEQUENCE: 34
gggaccggtg ccaccatgaa cgtctatatc accgccgac                                39

<210> SEQ ID NO 35
<211> LENGTH: 32
<212> TYPE: DNA
<213> ORGANISM: Artificial
<220> FEATURE:
<223> OTHER INFORMATION: Venus149C-C3 reverse primer

<400> SEQUENCE: 35
ggaagatctg acttgtacag ctcgtccatg cc                                       32
```

MAM-SPECIFIC FLUORESCENCE CALCIUM SENSOR AND USE THEREOF

REFERENCE TO AN ELECTRONIC SEQUENCE LISTING

The contents of the electronic sequence listing (sequence-listing.txt; Size: 44,282 bytes; and Date of Creation: Jun. 28, 2022) is herein incorporated by reference in its entirety.

TECHNICAL FIELD

The present disclosure relates to a Mitochondria-Associated endoplasmic reticulum Membrane (MAM)-specific fluorescent calcium sensor and a use thereof.

BACKGROUND ART

A calcium ion is one of important signal transduction materials participating in various physiological processes in cells. To sensitively operate a signaling system in response to a weak stimulus generated from the outside, cells dynamically regulate a calcium ion concentration in the cytosol, for example, by usually maintaining a low calcium ion concentration of approximately 100 nM, but rapidly increasing the concentration of calcium ions to 1 to 2 mM in stimulation to transfer a signal or make a rapid change in a specific microcompartment in cells, etc. To this end, cells have various types of calcium ion channels and calcium ion-sensitive signal transduction materials in cell membranes, organelles, etc.

Calcium ions enter into cells through a specific channel to operate a signaling system, and are immediately absorbed to organelles such as endoplasmic reticulum (ER), mitochondria, etc. In this process, the ER and mitochondria are known to serve as calcium ion reservoirs in cells, and play another pivotal role in a calcium ion signaling system.

Meanwhile, as the understanding of roles of organelles deepens, the presence of MAM, which is a contact site between the ER and mitochondria to directly exchange calcium ions, has been recently found. Today, it has been found that MAM is an important functional compartment having functions such as lipid exchange, transduction of a signaling material, etc., as well as calcium ion exchange, and that, in fact, main calcium ion channels such as inositol-1, 4,5-trisphosphate (IP3) receptors, ryanodine receptors, mitochondrial calcium uniporters, etc. are collected in MAM (Biochim Biophys. Acta., 2009. 1787(11): p. 1342-51). These results represent that both organelles, ER and mitochondria, play pivotal roles through a more direct interaction.

Although the presence and some functions of MAM have been revealed as mentioned above, there is no experimental technique useful for observing a microcompartment in which ER and mitochondria come very close to each other at a distance of approximately 10 to 25 nm. This is attributed to the physical properties of MAM, which is not clearly defined by membranes like the organelles such as mitochondria, ER, etc. and is dynamically regulated. Until now, there is little known about the MAM structure, a mechanism in which MAM can regulate transduction of a signaling material such as calcium ions, or a sensor that can sense the mechanism.

DISCLOSURE

Technical Problem

For this reason, the present inventors have conducted intensive studies to develop, by using physical properties of MAM formed by making a close contact between ER and mitochondria at a distance of 10 to 25 nm, a MAM-specific calcium ion sensor material which directly represents the migration of calcium ions through MAM by fluorescence, and thus devised the present disclosure.

Therefore, the present disclosure is directed to providing a MAM-specific fluorescent calcium sensor, which includes (a) a first fluorescent complementary structure in which a linker peptide and a fragment of a calcium ion-sensitive fluorescent sensor protein sequentially bind to a fragment of an ER-targeting protein, and (b) a second fluorescent complementary structure in which a linker peptide and a fragment of a calcium ion-sensitive fluorescent sensor protein sequentially bind to a fragment of a mitochondria-targeting protein.

However, technical problems to be solved in the present disclosure are not limited to the above-described problems, and other problems which are not described herein will be fully understood by those of ordinary skill in the art from the following descriptions.

Technical Solution

The present disclosure provides a MAM-specific fluorescent calcium sensor which includes the following structures:

(a) a first fluorescent complementary structure in which a linker peptide and a fragment of a calcium ion-sensitive fluorescent sensor protein sequentially bind to a fragment of an ER-targeting protein; and (b) a second fluorescent complementary structure in which a linker peptide and a fragment of a calcium ion-sensitive fluorescent sensor protein sequentially bind to a fragment of a mitochondria-targeting protein.

In one exemplary embodiment of the present disclosure, the ER-targeting protein may be suppressor of actin 1 (SAC1).

In another exemplary embodiment of the present disclosure, a fragment of the SAC1 protein consists of amino acids 521 to 587 of a full-length SAC1 protein.

In still another exemplary embodiment of the present disclosure, the mitochondria-targeting protein is A Kinase Anchoring Protein 1 (AKAP1).

In yet another exemplary embodiment of the present disclosure, a fragment of the AKAP1 protein consists of amino acids 34 to 63 of a full-length AKAP1 protein.

In yet another exemplary embodiment of the present disclosure, the mitochondria-targeting protein is Mitofusin 1 (MFN1).

In yet another exemplary embodiment of the present disclosure, the fragment of the SAC1 protein is encoded by a polynucleotide consisting of a base sequence of SEQ ID NO: 1.

In yet another exemplary embodiment of the present disclosure, the fragment of the AKAP1 protein is encoded by a polynucleotide consisting of a base sequence of SEQ ID NO: 2.

In yet another exemplary embodiment of the present disclosure, the MFN1 protein is encoded by a polynucleotide consisting of a base sequence of SEQ ID NO: 3.

In yet another exemplary embodiment of the present disclosure, the linker peptide is encoded by a polynucleotide including 1 to 8 repeats of a base sequence of SEQ ID NO: 4.

In yet another exemplary embodiment of the present disclosure, the linker peptide is encoded by a polynucleotide including 2 to 4 repeats of the base sequence of SEQ ID NO: 4.

In yet another exemplary embodiment of the present disclosure, the calcium ion-sensitive fluorescent sensor protein is a split GCaMP protein.

In yet another exemplary embodiment of the present disclosure, the split GCaMP protein is encoded by a polynucleotide consisting of a base sequence of SEQ ID NO: 5.

In yet another exemplary embodiment of the present disclosure, the split GCaMP protein is encoded by a polynucleotide consisting of a base sequence of SEQ ID NO: 6.

The present disclosure also provides an expression vector including a polynucleotide encoding the first fluorescent complementary structure.

The present disclosure also provides an expression vector including a polynucleotide encoding the second fluorescent complementary structure.

The present disclosure also provides a method of sensing MAM-specific calcium using the MAM-specific fluorescent calcium sensor.

Advantageous Effects

The present disclosure can provide a simple and accurate MAM-specific calcium ion sensor because it can overcome the limitation of a conventional method in that the phenomenon of calcium migration through MAM should be circumstantially explained by way of measuring a calcium ion concentration in each of ER and mitochondria and can exclude the influence of a variety of different calcium ion channels present in mitochondria on changes in calcium ions by directly measuring a concentration of calcium ions at a path through which calcium ions migrate.

DESCRIPTION OF DRAWINGS

FIG. 1A is a schematic diagram illustrating a process of designing a MAM-specific fluorescent calcium sensor of the present disclosure.

FIG. 1B is a schematic diagram illustrating a principle of operating a MAM-specific fluorescent calcium sensor of the present disclosure.

FIG. 2 is a schematic diagram illustrating a difference between a MAM-specific fluorescent calcium sensor of the present disclosure and a conventional method.

FIG. 3A is a schematic diagram illustrating a structure of an FOS/JUN leucin zipper-inserted nucleic acid molecule for experimental verification.

FIG. 3B is a schematic diagram illustrating splitting points in candidate genes for split GCaMP of the present disclosure.

FIG. 4 shows the fluorescent reactivity of split GCaMP with respect to calcium ion stimulation, expressed by candidate genes for the split GCaMP of the present disclosure.

FIG. 5 shows the reactivity of spGCaMP144/149, which is the most effective combination among the split GCaMP candidate group of the present disclosure, with respect to calcium ion stimulation taken by a time-lapse imaging technique, and numerical quantification thereof.

FIG. 6A shows recombinant expression vectors for a MAM-specific fluorescent marker of the present disclosure.

FIG. 6B shows recombinant expression vectors for a MAM-specific fluorescent marker of the present disclosure.

FIG. 7A shows a result of comparing intracellular fluorescent patterns between a MAM-specific fluorescent marker of the present disclosure and conventional ER/mitochondrial fluorescent markers to confirm the effectiveness of the MAM-specific fluorescent marker of the present disclosure.

FIG. 7B shows a result of analyzing Mander's colocalization coefficients thereof.

FIG. 7C shows results of fluorescent line analysis thereof.

FIG. 8A shows recombinant expression vectors of fluorescent complementary structures constituting a MAM-specific fluorescent calcium sensor of the present disclosure.

FIG. 8B shows recombinant expression vectors of fluorescent complementary structures constituting a MAM-specific fluorescent calcium sensor of the present disclosure.

FIG. 9 shows the reactivity of the recombinant expression vector of FIG. 8 with respect to calcium ion stimulation, taken by a time-lapse imaging technique, after the recombinant expression vector is transfected to HEK293 cells, and numerical quantification of the reactivity.

MODES OF THE DISCLOSURE

The present disclosure provides a MAM-specific fluorescent calcium sensor, which includes (a) a first fluorescent complementary structure in which a linker peptide and a fragment of a calcium ion-sensitive fluorescent sensor protein sequentially bind to a fragment of an ER-targeting protein, and (b) a second fluorescent complementary structure in which a linker peptide and a fragment of a calcium ion-sensitive fluorescent sensor protein sequentially bind to a fragment of a mitochondria-targeting protein (refer to FIGS. 1A and 1B).

Conventionally, since genetic materials capable of measuring a concentration of calcium ions have been found, many research groups have conducted studies to measure a calcium concentration in a specific organelle in cells by applying various genetic methods and focusing on organelles having a membrane structure, such as the ER, mitochondria, a lysosome, etc.

For example, to measure the migration of calcium ions through MAM as a main path of transferring calcium ions between the ER and mitochondria and an increase in calcium ion concentration in mitochondria thereby, there is a method of estimating the migration of calcium ions through MAM by measuring changes in calcium concentration in each of the ER and mitochondria using an ER-targeting fluorescent calcium ion sensor protein and an mitochondria-targeting fluorescent calcium ion sensor protein and then collectively using the measurement results (refer to FIG. 2).

However, this method not only should be performed by several steps, but also is unable to directly prove that the delivery of calcium ions in the ER to the mitochondria is specifically "through MAM" among a plurality of mitochondrial calcium ion paths, and the only thing that this method can prove accurately is introduction of calcium ions into the mitochondria. That is, since, due to characteristics of the ER and mitochondria in which various calcium ion channels besides MAM are present, the possibility that the migration of calcium ions is achieved through a channel other than MAM cannot be excluded, there is a limitation in that the migration of calcium ions through MAM cannot be directly proved.

In the present disclosure, a biomolecular fluorescence complementation (BiFC) system is a tool for analyzing the fluorescence exhibited when a complete fluorescent protein is formed, wherein protein fragment complementation is applied to a fluorescent protein, the fluorescent protein is then divided into N-terminus and C-terminus fragments and expressed with each one of two proteins whose mutual interaction is to be investigated, and then the two proteins come close to each other for interaction, the two fragments of the fluorescent protein are combined, thereby forming a complete fluorescent protein, and the present disclosure is the first to introduce such BiFC technique for MAM-specific fluorescent calcium sensing.

In the present disclosure, an ER-targeting protein constituting a first fluorescent complementary structure has no particular limit as long as it can specifically target the ER, and may be, for example, annexin or an inositol 1,4,5-triphosphate receptor (IP3R), and preferably suppressor of actin 1 (SAC1).

Here, a fragment of the SAC1 protein may consist of amino acids 521 to 587 of a full-length SAC1 protein, and may be encoded by a polynucleotide consisting of a base sequence of SEQ ID NO: 1, or a base sequence having at least 60%, 70%, 80%, 90% or 95% homology therewith.

In the present disclosure, a mitochondria-targeting protein constituting the second fluorescent complementary structure does not have a particular limitation as long as it can specifically target mitochondria, and may be, for example, translocase of outer mitochondrial membrane 20 (TOM20) or voltage dependent anion channel 1 (VDAC1), and preferably A Kinase Anchoring Protein 1 (AKAP1) or Mitofusin 1 (MFN1).

Here, a fragment of the AKAP1 protein may consist of amino acids 34 to 63 of a full-length AKAP1 protein, and may be encoded by a polynucleotide consisting of a base sequence of SEQ ID NO: 2, or a base sequence having at least 60%, 70%, 80%, 90% or 95% homology therewith. In addition, the MFN1 protein may be encoded by a polynucleotide consisting of a base sequence of SEQ ID NO: 3, or a base sequence having at least 60%, 70%, 80%, 90% or 95% homology therewith.

In the present disclosure, the linker peptide has no limit as long as it can link the targeting protein to the split GCaMP, and may be encoded by a polynucleotide including 1 to 8 repeats, preferably 2 to 4 repeats, of a base sequence of SEQ ID NO: 4 or a base sequence having at least 60%, 70%, 80%, 90% or 95% homology therewith.

Here, the term "percent sequence homology" refers to a degree of identity between a randomly given sequence and a target sequence.

In the present disclosure, the calcium ion-sensitive fluorescent sensor protein is a fluorescent protein which can be used in BiFC analysis for analyzing protein-protein interaction, dimerization or oligomerization in cells, and the type of the calcium ion-sensitive fluorescent sensor protein is not particularly limited as long as it can measure fluorescence produced in response to calcium ions. The calcium ion-sensitive fluorescent sensor protein is preferably GCaMP, PeriCaM or Cameleon, and is designed with various sizes according to the type, characteristic, stability or fluorescence intensity of a protein.

More preferably, the calcium ion-sensitive fluorescent sensor protein is a fluorescent calcium indicator (GCaMP) fragment encoded by a polynucleotide consisting of a base sequence of SEQ ID NO: 5 or 6. The GCaMP is a calcium ion-sensitive fluorescent sensor protein having a structure in which Calmodulin, which transforms in response to calcium ions, is fused with a green fluorescent protein (GFP).

In addition, the present disclosure provides a recombinant expression vector which expresses an ER- or mitochondria-targeting protein as a fusion protein with a fluorescent protein via a linker peptide.

The "vector" used herein may be any material which can deliver or express a nucleic acid molecule in a host cell or a test specimen. Accordingly, the vector may be a replicon, for example, a plasmid, a phage or a cosmid, into which a PCR product or any nucleic acid segment which is introduced into cells and integrated into a cell genome can be inserted. Generally, a vector may be replicated when binding to a suitable regulatory element. A vector backbone suitable for being used in the present disclosure may be manufactured to be expressed by a promoter showing high expression efficiency in mammalian cells, and may include, for example, a CMV promoter. Preferably, pEGFP-N1 and pEGFP-C3 vectors disclosed in FIGS. 6A and 6B are used as a backbone.

In the present disclosure, there is no limit to a method of manufacturing a fusion gene by cloning a desired gene to the vector backbone, and the method may be, for example, blunt-ended termini or stagger-ended termini for ligation, digestion with a restriction enzyme for providing suitable termini, ligation of cohesive ends as needed, treatment with an alkaline phosphatase to avoid unfavorable bonding, and enzyme ligation.

In the present disclosure, the targeting protein-linker peptide is expressed in the form of a fusion protein expressed as one polypeptide by peptide bonding with the N- or C-terminus region of a calcium ion-sensitive fluorescent sensor protein, and since the linker peptide may bind to both the C-terminus or the N-terminus of the fluorescent protein, the targeting protein-linker peptide may be expressed in the form of (calcium ion-sensitive fluorescent sensor protein terminus region)-linker or linker-(calcium ion-sensitive fluorescent sensor protein terminus region).

In the present disclosure, it can be confirmed that by transfecting cells with a recombinant expression vector of the present disclosure and culturing the same to express a protein in the cells, and measuring fluorescence in response to MAM-specific calcium, it is possible to target a specific location in the cells and accurately analyze a protein-protein interaction. Here, fluorescence may be measured using a fluorescence microscope, a confocal microscope, etc.

In addition, the present disclosure may provide a method of measuring a MAM-specific calcium concentration by sensing MAM-specific calcium using the MAM-specific fluorescent calcium sensor.

Hereinafter, to help in understanding the present disclosure, exemplary examples will be proposed. However, the following examples are merely provided to more easily understand the present disclosure, and not to limit the present disclosure.

EXAMPLES

Example 1. Construction of Split GCaMP 1-1. Insertion of Leucine Zipper Sequence for Experimental Verification ① Fos Leucine Zipper A leucine zipper sequence (the 279 bp gene sequence corresponding to the sequence of amino acids 118 to 210) of a mouse Fos gene (FBJ osteosarcoma oncogene, *Mus musculus*, Gene ID: 14281) was amplified based on a pEGFP-C3 vector and inserted as a Fos leucine zipper sequence of a recombinant gene.

To this end, a mouse cDNA library was used as a template and subjected to PCR using the following primers.

```
Fos-(118aa-210aa) forward primer:
                                    (SEQ ID NO: 10)
5'-CCG GGA ATT CTG GGC AGA GCG CAG AGC ATC G-3'
```

Fos-(118aa-210aa) reverse primer:
(SEQ ID NO: 11)
5'-CGC GGA TCC TCA AAG GTC ATC GGG GAT CTT GCA G-3'

The amplified DNA was treated with EcoR I and BamH I restriction enzymes and then inserted into a pEGFP-C3 vector subjected to cleavage with EcoR I and BamH I restriction enzymes using a T4 ligase, thereby constructing a pEGFP-C3-Fos(118aa-210aa) vector.

② Jun Leucine Zipper

To construct a Jun leucine zipper sequence vector which can interact with the Fos leucine zipper sequence, a leucine zipper sequence (the 186 bp gene sequence corresponding to the sequence of amino acids 257 to 318) of a mouse Jun gene (Jun protooncogene, *Mus musculus*, Gene ID: 16476) was amplified based on a pEGFP-C3 vector and inserted as a Jun leucine zipper sequence of a recombinant gene.

To this end, a mouse cDNA library was used as a template and subjected to PCR using the following primers.

Jun-(257aa-318aa) forward primer:
(SEQ ID NO: 12)
5'-CCG GAA TTC TGA AGG CAG AGA GGA AGC GCA TG-3'

Jun-(257aa-318aa) reverse primer:
(SEQ ID NO: 13)
5'-CGC GGA TCC TCA GTG GTT CAT GAC TTT CTG-3'

The amplified DNA was treated with EcoR I and BamH I restriction enzymes and then inserted into a pEGFP-C3 vector previously subjected to cleavage with EcoR I and BamH I restriction enzymes using a T4 ligase, thereby constructing a pEGFP-C3-Jun(257aa-318aa) vector.

1-2. Construction of Candidate Split GCaMP Gene

Based on known GCaMP6s sequence and an enhanced GFP (EGFP) structure, to deduce the optimal combination of split GCaMP genes exhibiting fluorescence and calcium ion reactivity of GCaMP, four types of recombinant vectors for 7 split GCaMP genes were constructed as follows.

In each combination, a gene corresponding to the amino terminus (N-terminus) of the protein sequence of GCaMP was replaced with an EGFP gene of a pEGFP-C3-Fos (118aa-210aa) vector, and a gene corresponding to the carboxy terminus (C-terminus) was replaced with an EGFP gene of a pEGFP-C3-Jun(257aa-318aa) vector (refer to FIGS. 3A and 3B).

Combination 1 (balanced pair)
(spGC149)-Fos(118aa-210aa) vector
spGC-N-terminus forward primer:
(SEQ ID NO: 14)
5'-gggaccggtgccaccatgggttctcatcatcatcatcatg-3' spGC149 reverse primer:
(SEQ ID NO: 15)
5'-ggaagatctgacttgtacagctcgtccatgcc-3'

(spGC144)-Jun(257aa-318aa) vector
spGC144 forward primer:
(SEQ ID NO: 16)
5'-gggaccggtgccaccatggtgagcaagggcgag-3' spGC-C-terminus reverse primer:
(SEQ ID NO: 17)
5'-ggaagatctgacttcgctgtcatcatttgtacaaac-3'

Combination 2 (unbalanced pair #1)
(spGC100)-Fos(118aa-210aa) vector
spGC-N-terminus forward primer:
(SEQ ID NO: 14)
5'-gggaccggtgccaccatgggttctcatcatcatcatcatg-3' spGC100 reverse primer:
(SEQ ID NO: 18)
5'-ggaagatctgagaagaagatggtgcgctcctg-3'

(spGC105)-Jun(257aa-318aa) vector
spGC105 forward primer:
(SEQ ID NO: 19)
5'-gggaccggtgccaccatgtacaagacccgcgccgag-3' spGC-C-terminus reverse primer:
(SEQ ID NO: 17)
5'-ggaagatctgacttcgctgtcatcatttgtacaaac-3'

Combination 3 (unbalanced pair #2-1)
(spGC188)-Fos(118aa-210aa) vector
spGC-N-terminus forward primer:
(SEQ ID NO: 14)
5'-gggaccggtgccaccatgggttctcatcatcatcatcatg-3' spGC188 reverse primer:
(SEQ ID NO: 20)
5'-ggaagatctgagatgggggtgttctgctgg-3'

(spGC172)-Jun(257aa-318aa) vector
spGC172 forward primer:
(SEQ ID NO: 21)
5'-gggaccggtgccaccatggacggcggcgtgcagc-3' spGC-C-terminus reverse primer:
(SEQ ID NO: 17)
5'-ggaagatctgacttcgctgtcatcatttgtacaaac-3'

Combination 4 (unbalanced pair #2-2)
(spGC188)-Fos(118aa-210aa) vector
spGC-N-terminus forward primer:
(SEQ ID NO: 14)
5'-gggaccggtgccaccatgggttctcatcatcatcatcatg-3' spGC188 reverse primer:
(SEQ ID NO: 20)
5'-ggaagatctgagatgggggtgttctgctgg-3'

(spGC199)-Jun(257aa-318aa) vector
spGC199 forward primer:
(SEQ ID NO: 22)
5'-gggaccggtgccaccatgcactacctgagcgtgcagtcc-3' spGC-C-terminus reverse primer:
(SEQ ID NO: 17)
5'-ggaagatctgacttcgctgtcatcatttgtacaaac-3'

The GCaMP6s gene was used as a template and subjected to DNA amplification with each of the above-listed combinations of corresponding primers. Subsequently, the amplified DNA was treated with Age I and Bgl II restriction enzymes. The DNA subjected to treatment with the restriction enzymes was inserted into each of a pEGFP-C3-Fos (118aa-210aa) vector and a pEGFP-C3-Jun(257aa-318aa) vector from which an EGFP gene part was removed using Age I and Bgl II restriction enzymes. Here, a T4 ligase was used.

Example 2. Confirmation of Calcium Reactivity of Split GCaMP 2-1. Transfection of Recombinant Vector HEK293 cells cultured on a glass-bottomed dish for 12 hours were transfected with the four gene combinations constructed in Example 1, using a lipofectamine 2000 reagent in accordance with a manufacturer's protocol.

2-2. Real-Time Observation Using Fluorescence Microscope

After the transfection, HEK293 cells were cultured in 10% fetal bovine serum (FBS)-containing DMEM under conditions of 37° C. and 5% $CO_2$ for 24 hours, and then the medium was replaced with a calcium-free imaging buffer (145 mM NaCl, 2.5 mM KCl, 10 mM glucose, 10 mM HEPES pH 7.4, 1 mM $MgCl_2$), followed by a time-lapse imaging test performed using a fluorescence microscope every second.

As stimuli for a calcium reaction, ionomycin (Sigma-Aldrich) and a $CaCl_2$ aqueous solution were treated to have a final working concentration of 10 μM and 1 mM, respectively.

As a result, as shown in FIG. 4, the combination of spGCaMP144 and spGCaMP149 among the four bimolecular combinations of split GCaMP was identified as the optimal combination exhibiting green fluorescence in response to calcium ions in the same manner as the conventional GCaMP.

In addition, the reactivity to calcium ions in cells transfected with a (spGC149)-Fos(118aa-210aa) vector and a (spGC144)-Jun(257aa-318aa) vector was investigated by time-lapse fluorescent microscopy. Here, time-lapse fluorescent microscopy was used to observe a time-lapse fluorescence change every 10 seconds for total of approximately 150 seconds. The Fos(118aa-210aa) and Jun(257aa-318aa) sequences used in Example 1 were used to target all of GCaMP and BiFC used herein to a nucleus, GCaMP used as a single molecule was nuclear specifically targeted by linkage with 3 repeats of the NLS sequence, and the GCaMP-NLS sequence is represented by SEQ ID NO: 7.

As a result, as shown in FIG. 5, it was confirmed that the combination of spGCaMP144 and spGCaMP149 can be used as a bimolecular fluorescent calcium sensor which has reactivity at a similar level to that of GCaMP6 being widely used and can produce fluorescence in response to calcium ions only when the members of the combination are in proximity to each other.

Example 3. Construction of MAM-Specific Recombinant Nucleic Acid Molecule 3-1. Construction of Mitochondria-Targeting, Recombinant Nuclear Acid Molecule Using AKAP1

① Insertion of Mitochondria-Targeting Sequence

A mitochondria-targeting sequence (the 90 bp gene sequence corresponding to the sequence of amino acids 34 to 63) of a mouse Akap1 gene (A kinase (PRKA) anchor protein 1, Mus musculus, Gene ID: 11640) was amplified using a pEGFP-N1 vector, thereby constructing a mitochondria-targeting vector.

To this end, a mouse cDNA library was used as a template and subjected to PCR using primers of the following sequences.

```
AKAP1-(34aa-63aa) forward primer:
                                (SEQ ID NO: 23)
5'-ctagctagccaccatggcaatccagagcgttcg-3'

AKAP1-(34aa-63aa) reverse primer:
                                (SEQ ID NO: 24)
5'-ccgctcgagttattacgagagaaaaaccaccaccagcc-3'
```

The amplified DNA was treated with Nhe I and Xho I restriction enzymes and inserted into a pEGFP-N1 vector that were previously subjected to cleavage with Nhe I and Xho I restriction enzymes using a T4 ligase, thereby constructing a pEGFP-N1-AKAP1(34aa-63aa) vector.

② Replacement of Fluorescent Protein Gene

A Venus gene was used as a template and subjected to PCR using the following primers.

```
Venus155-N1 forward primer:
                                (SEQ ID NO: 25)
5'-cgcggatcccaccatgaagcagaagaacggcatcaag-3'

Venus155-N1 reverse primer:
                                (SEQ ID NO: 26)
5'-aaatatgcggccgctttacttgtacagctcgtccatgc-3'
```

The amplified gene was treated with BamH I and Not I restriction enzymes and then inserted, using a T4 ligase, into a pEGFP-N1-AKAP1(34aa-63aa) vector previously treated with BamH I and Not I restriction enzymes to truncate an EGFP gene part, thereby constructing a pVenus(155-C)-N1-AKAP1(34aa-63aa) vector in which the EGFP gene was replaced with a BiFC gene.

③ Insertion of Linker Sequence

The following 60 bp linker sequence was used independently, or repeats thereof were used as needed.

```
linker sequence:
                                (SEQ ID NO: 4)
5'-gacccaaccaggtcagcgaattctggagcaggagcaggagcag gagcaatactctcccgt-3'
```

Specifically, a linker sequence having the following sequence was synthesized, and the synthesized oligo DNA was treated with Xho I and Sal I restriction enzymes and inserted into a pVenus(155-C)-N1-AKAP1(34aa-63aa) vector previously treated with a Xho I restriction enzyme using a T4 ligase, thereby constructing a pVenus(155-C)-linker-AKAP1(34aa-63aa) vector (refer to FIG. 6A).

```
linker oligo DNA:
                                (SEQ ID NO: 27)
5'-ccgctcgag (gacccaaccaggtcagcgaattctggagcaggagcaggagca atactctcccgt)n gtcgac-3'
```

3-2. Construction of Mitochondria-Targeting, Recombinant Nucleic Acid Molecule Using MFN1

① Insertion of Mitochondria-Targeting Sequence

A mouse Mfn1 gene (Mitofusin 1, Mus musculus, Gene ID: 67414) was amplified using a pEGFP-C3 vector, thereby constructing a mitochondria-targeting vector.

To this end, a mouse cDNA library was used as a template and subjected to PCR using primers having the following sequences.

```
MFN1 forward primer:
                                (SEQ ID NO: 28)
5'-ccggaattctggcagaaacggtatctccactgaag-3'

MFN1 reverse primer:
                                (SEQ ID NO: 29)
5'-cgcggatccttaggattctccactgctcggg-3'
```

The amplified DNA was treated with EcoR I and BamH I restriction enzymes and inserted into a pEGFP-C3 vector previously subjected to cleavage with EcoR I and BamH I restriction enzymes using a T4 ligase, thereby constructing a pEGFP-C3-MFN1 vector.

② Replacement of Fluorescent Protein Gene

A Venus gene was used as a template and subjected to PCR using the following primers.

```
Venus N172-C3 forward primer:
                                    (SEQ ID NO: 30)
5'-gggaccggtgccaccatggtgagcaagggcgag-3'

Venus N172-C3 reverse primer:
                                    (SEQ ID NO: 31)
5'-ggaagatctgactcgatgttgtggcggatc-3'
```

The amplified DNA was treated with Age I and Bgl II restriction enzymes, and then inserted into a pEGFP-C3-MFN1 vector previously treated with Age I and Bgl II restriction enzymes to cleave an EGFP gene using a T4 ligase, thereby constructing a pVenus(N-172)-C3-MFN1 vector in which an EGFP gene was replaced with a BiFC gene.

③ Insertion of Linker Sequence

Similarly as in Example 3-1, a 60 bp linker sequence was used independently, or repeats thereof were used as needed, and an oligo DNA synthesized by the same method as used in Example 3-1 was treated with Xho I and Sal I restriction enzymes and inserted into a pVenus(N-172)-C3-MFN1 vector previously treated with an Xho I restriction enzyme using a T4 ligase, thereby constructing a pVenus(N-172)-linker-MFN1 vector (refer to FIG. 6B).

```
linker oligo DNA:
                                    (SEQ ID NO: 27)
5'-ccgctcgag (gacccaaccaggtcagcgaattctggagcaggagcaggagcaggagca atactctcccgt)n gtcgac-3'
```

3-3. Construction of ER-Targeting, Recombinant Nucleic Acid Molecule Using SAC1

① Insertion of ER-Targeting Sequence

An ER-targeting sequence (the 204 bp gene sequence corresponding to the sequence of amino acids 521 to 587) of a mouse Sac 1 gene (suppressor of actin mutations 1 (SAC1)-like (yeast), *Mus musculus*, Gene ID: 83493) was amplified using a pEGFP-C3 vector and then inserted as an ER-targeting sequence of a recombinant gene.

To this end, a mouse cDNA library was used as a template and subjected to PCR using the following primers.

```
SAC1-(521aa-587aa) forward primer:
                                    (SEQ ID NO: 32)
5'-cggggtaccgttcctggcgttgcctatcatc-3'

SAC1-(521aa-587aa) reverse primer:
                                    (SEQ ID NO: 33)
5'-cgcggatcctcagtctatcttttctttctggaccag-3'
```

The amplified DNA was treated with Kpn I and BamH I restriction enzymes and then inserted into a pEGFP-C3 vector previously subjected to cleavage with Kpn I and BamH I restriction enzymes using a T4 ligase, thereby constructing a pEGFP-C3-SAC1(521aa-587aa) vector.

② Replacement of Fluorescent Protein Gene

A Venus gene was used as a template and subjected to PCR using the following primers.

```
Venus149C-C3 forward primer:
                                    (SEQ ID NO: 34)
5'-gggaccggtgccaccatgaacgtctatatcaccgccgac-3'

Venus149C-C3 reverse primer:
                                    (SEQ ID NO: 35)
5'-ggaagatctgacttgtacagctcgtccatgcc-3'
```

The amplified gene was treated with Age I and Bgl II restriction enzymes and then inserted, using a T4 ligase, into a pEGFP-C3-SAC1(521aa-587aa) vector previously treated with Age I and Bgl II restriction enzymes to truncate an EGFP gene part, thereby constructing a pVenus(149-C)-C3-SAC1(521aa-587aa) vector in which the EGFP gene is replaced with a BiFC gene.

③ Insertion of Linker Sequence

Similarly as in Example 3-1, a 60 bp linker sequence was used independently, or repeats thereof were used as needed, and an oligo DNA synthesized by the same method as used in Example 3-1 was treated with Xho I and Sal I restriction enzymes and inserted into a pVenus(149-C)-C3-SAC1 (521aa-587aa) vector previously treated with an Xho I restriction enzyme using a T4 ligase, thereby constructing a pVenus(149-C)-linker-SAC1(521aa-587aa) vector (refer to FIG. 6B).

3-4. Verification of MAM Targeting

① Preparation and Observation of Sample for Microscopy

To verify MAM targeting of the bimolecular MAM-specific fluorescent marker prepared in the present disclosure, HEK293 cells were transfected with the constructed pVenus(N-172)-linker-MFN1 vector, pVenus(149-C)-linker-SAC1(521aa-587aa) vector and a mitochondrial or ER fluorescent marker gene vector, thereby preparing a microscope sample.

Afterward, as a result of observing an intracellular fluorescence pattern using a fluorescence microscope, as shown in FIG. 7A, it was confirmed that a MAM-specific biomolecular fluorescent marker using these targeting sequences in cells selectively targets the contact site between the ER and mitochondria (MAM).

② Analysis of MAM Targeting

To analyze a MAM targeting level of the bimolecular MAM-specific fluorescent marker constructed in the present disclosure, the fluorescent images taken using the prepared microscope samples were analyzed using Image J, which is the software for universal image analysis distributed by NIH.

First, according to a method used in conventional MAM research, an overlapping spot in fluorescence of an ER-targeting fluorescent material labeling an ER matrix and a mitochondria-targeting fluorescent material labeling a mitochondrial matrix was extracted, and used for determining the Mander's colocalization coefficient with a fluorescence pattern of a biomolecular MAM-specific fluorescent marker.

As a result, as shown in FIG. 7B, it was confirmed that, in all investigated cells, the bimolecular MAM-specific fluorescent marker of the present disclosure exhibits fluorescence at a higher level at the overlapping spot (overlapped) in which fluorescence of mitochondria and ER are overlapped than each of the mitochondrial and ER fluorescent markers.

In addition, line analysis was performed to analyze patterns of a MAM-specific fluorescent marker, an ER fluorescent marker, and a mitochondrial fluorescent marker in a section in which a MAM-specific fluorescent signal is detected.

As a result, as shown in FIG. 7C, it was confirmed that the MAM-specific biomolecular fluorescent marker of the present disclosure very accurately labels MAM present at a boundary (a region in which solid lines of the graph intersect, indicated by arrow) between mitochondria (blue fluorescence) and ER (red fluorescence).

Example 4. Construction of MAM-Specific Calcium Ion Sensor Recombinant Expression Vector Based on the pVenus(155-C)-linker-AKAP1(34aa-63aa) vector constructed in Example 3, a GCaMP6s gene was used as a template and subjected to PCR amplification using the following primers used in Combination 1 of Example 1-2.

```
spGC144 forward primer:
                                      (SEQ ID NO: 16)
5'-gggaccggtgccaccatggtgagcaagggcgag-3' spGC-C-terminus reverse primer:
                                      (SEQ ID NO: 17)
5'-ggaagatctgacttcgctgtcatcatttgtacaaac-3'
```

Afterward, the PCR product was treated with BamH I and Not I restriction enzymes and inserted, using a T4 ligase, into a pVenus(155-C)-linker-AKAP1(34aa-63aa) vector which was previously treated with BamH I and Not I restriction enzymes to truncate a Venus(155-C) gene part, thereby constructing an AKAP1(34aa-63aa)-linker-spGC144 vector (refer to FIG. 8A).

Likewise, based on the pVenus(N-172)-linker-MFN1 vector constructed in Example 3, a GCaMP6s gene was used as a template and subjected to PCR amplification using the following primers used in Combination 1 of Example 1-2.

```
spGC144 forward primer:
                                      (SEQ ID NO: 16)
5'-gggaccggtgccaccatggtgagcaagggcgag-3' spGC-C-terminus reverse primer:
                                      (SEQ ID NO: 17)
5'-ggaagatctgacttcgctgtcatcatttgtacaaac-3'
```

Afterward, the PCR product was treated with Age I and Bgl II restriction enzymes and inserted, using a T4 ligase, into a pVenus(N-172)-linker-MFN1 vector which was previously treated with Age I and Bgl II restriction enzymes to truncate a Venus(N-172) gene part, thereby constructing a spGC144-linker-MFN1 vector.

In addition, based on the pVenus(149-C)-linker-SAC1 (521aa-587aa) vector constructed in Example 3, a GCaMP6s gene was used as a template and subjected to PCR amplification using the following primers used in Combination 1 of Example 1-2.

```
spGC-N-terminus forward primer:
                                      (SEQ ID NO: 14)
5'-gggaccggtgccaccatgggttctcatcatcatcatcatcatg-3'
```

```
spGC149 reverse primer:
                                      (SEQ ID NO: 15)
5'-ggaagatctgacttgtacagctcgtccatgcc-3'
```

Afterward, the PCR product was treated with Age I and Bgl II restriction enzymes and inserted, using a T4 ligase, into a pVenus(149-C)-linker-SAC1(521aa-587aa) vector which was previously treated with Age I and Bgl II restriction enzymes to truncate a Venus(149-C) gene part, thereby constructing a spGC149-linker-SAC1(521aa-587aa) vector.

Example 5. Confirmation of Calcium Reactivity of MAM-Specific Calcium Ion Sensor Protein 5-1. Transfection of Recombinant Gene Vector HEK293 cells cultured on a glass-bottomed dish for 12 hours were transfected with each of the AKAP1(34aa-63aa)-linker-spGC144 vector and the spGC149-linker-SAC1 (521aa-587aa) vector, which were the recombinant expression vectors constructed in Example 4, using a lipofectamine 2000 reagent in accordance with a manufacturer's protocol.

5-2. Real-Time Observation Using Fluorescence Microscope

After the transfection, HEK293 cells were cultured in DMEM containing 10% Fetal Bovine Serum (FBS) under conditions of 37° C. and 5% $CO_2$ for 24 hours, the culture medium was replaced with a calcium-free imaging buffer (145 mM NaCl, 2.5 mM KCl, 10 mM glucose, 10 mM HEPES pH 7.4, 1 mM $MgCl_2$), and then a time-lapse imaging experiment was performed every second using a fluorescence microscope.

Ionomycin (Sigma-Aldrich) and inositol-1,4,5-trisphosphate (IP3) were used for treatment as stimuli for a MAM-specific calcium reaction to have a final working concentration of 10 μM, or $CaCl_2$ was used for treatment as a stimulus for a MAM-specific calcium reaction to have a final working concentration of 1 mM.

As a result, as shown in FIG. 9, it was confirmed that the MAM-specific calcium ion sensor protein (MAM-spGCaMP) expressed in the HEK293 cells can detect a calcium change in practice, as suggested by an increase in fluorescence upon treatment with IP3 or $CaCl_2$.

It would be understood by those of ordinary skill in the art that the above description of the present disclosure is exemplary, and the exemplary embodiments disclosed herein can be easily modified into other specific forms without departing from the technical spirit or making changes to essential features of the present disclosure. Therefore, the exemplary embodiments described above should be interpreted as illustrative and not limiting in any aspect.

INDUSTRIAL APPLICABILITY

With the MAM-specific calcium ion sensor according to the present disclosure, a change in calcium ion can be simply and accurately confirmed by directly measuring a calcium concentration at a path through which calcium ions are migrated, thus conventional limitations can be overcome, and the sensor can be useful in various basic and clinical studies by sensing a change in calcium ions in an organism.

The invention claimed is:

1. A Mitochondria-Associated endoplasmic reticulum Membrane(MAM)-specific fluorescent calcium sensor comprising the following structures: (a) a first fluorescent complementary structure in which a linker peptide and a fragment of a calcium ion-sensitive fluorescent sensor protein sequentially bind to a fragment of an Endoplasmic Reticulum(ER)-targeting protein, and (b) a second fluorescent complementary structure in which a linker peptide and a fragment of a calcium ion-sensitive fluorescent sensor protein sequentially bind to a fragment of a mitochondria-targeting protein, wherein the calcium ion-sensitive fluorescent sensor protein bound to the fragment of the Endoplasmic Reticulum(ER)-targeting protein is a split GCaMP protein which is encoded by a polynucleotide consisting of a base sequence of SEQ ID NO: 6, and wherein the calcium ion-sensitive fluorescent sensor protein bound to the fragment of the mitochondria-targeting protein is a split GCaMP protein which is encoded by a polynucleotide consisting of a base sequence of SEQ ID NO: 5.

2. The sensor according to claim 1, wherein the ER-targeting protein is suppressor of actin 1 (SAC1).

3. The sensor according to claim 2, wherein a fragment of the SAC1 protein consists of amino acids 521 to 587 of a full-length SAC1 protein.

4. The sensor according to claim 1, wherein the mitochondria-targeting protein is A Kinase Anchoring Protein 1(AKAP1).

5. The sensor according to claim 4, wherein a fragment of the AKAP1 protein consists of amino acids 34 to 63 of a full-length AKAP1 protein.

6. The sensor according to claim 1, wherein the mitochondria-targeting protein is Mitofusin 1(MFN1).

7. The sensor according to claim 3, wherein the fragment of the SAC1 protein is encoded by a polynucleotide consisting of a base sequence of SEQ ID NO: 1.

8. The sensor according to claim 5, wherein the fragment of the AKAP1 protein is encoded by a polynucleotide consisting of a base sequence of SEQ ID NO: 2.

9. The sensor according to claim 6, wherein the MFN1 protein is encoded by a polynucleotide consisting of a base sequence of SEQ ID NO: 3.

10. The sensor according to claim 1, wherein the linker peptide is encoded by a polynucleotide consisting of 1 to 8 repeats of a base sequence of SEQ ID NO: 4.

11. The sensor according to claim 10, wherein the linker peptide is encoded by a polynucleotide consisting of 2 to 4 repeats of the base sequence of SEQ ID NO: 4.

12. A method of sensing Mitochondria-Associated endoplasmic reticulum Membrane (MAM)-specific calcium using the sensor of claim 1.

* * * * *